United States Patent
Rosenmeier

(10) Patent No.: US 8,394,355 B2
(45) Date of Patent: Mar. 12, 2013

(54) USE OF UTP FOR THE DIAGNOSIS OF STENOSES AND OTHER CONDITIONS OF RESTRICTED BLOOD FLOW

(75) Inventor: Jaya Brigitte Rosenmeier, Hellerup (DK)

(73) Assignee: P2 science Aps (DK)

( * ) Notice: Subject to any disclaimer, the term of this patent is extended or adjusted under 35 U.S.C. 154(b) by 187 days.

(21) Appl. No.: 12/854,146

(22) Filed: Aug. 10, 2010

(65) Prior Publication Data

US 2011/0085977 A1    Apr. 14, 2011

Related U.S. Application Data

(60) Provisional application No. 61/232,518, filed on Aug. 10, 2009, provisional application No. 61/357,857, filed on Jun. 23, 2010.

(51) Int. Cl.
*A61K 49/00* (2006.01)

(52) U.S. Cl. ............... 424/9.1; 514/49; 514/50; 514/51

(58) Field of Classification Search .................. None
See application file for complete search history.

(56) References Cited

FOREIGN PATENT DOCUMENTS
EP    1 415 995 A2    5/2004

OTHER PUBLICATIONS

"UTP reduces infarct size and improves mice heart function after myocardial infarct via P2Y2 receptor," Cohen, r., et al., Biochemical Pharmacology 82: 1126-1133 (2011).*
Sigma-Aldrich catalog listing for UTP (available at http://www.sigmaaldrich.com/catalog/search?interface=All&term=UTP&lang=en&region=US&focus=product&N=0+220003048+2 19853269+219853286&mode=match%20partialmax), as retrieved Sep. 27, 2012.*
The International Search Report and the Written Opinion of the International Searching Authority for corresponding International Patent Application No. PCT/EP2010/061647, dated Nov. 29, 2010.
Seye, C. et al. "Functional $P2Y_2$ Nucleotide Receptors Mediate Uridine 5'-Triphosphate-Induced Intimal Hyperplasia in Collared Rabbit Carotid Arteries", Circulation, vol. 106, No. 21, Nov. 19, 2002, pp. 2720-2726.
Peter, A. et al. "Poster Presentations Poster PW024 Fractional functional reserve findings compared to myocardial perfusion imaging results", European Journal of Nuclear Medicine and Molecular Imaging, vol. 36, No. 2, Aug. 8, 2009, pp. S285.
Satta, J. et al. "Progression of Human Aortic Valve Stenosis Is Associated With Tenascin-C Expression", Journal of the American College of Cardiology, vol. 39, No. 1, Jan. 2, 2002, pp. 96-101.
Rosenmeier, J. et al. "Activation of ATP/UTP-selective receptors increases blood flow and blunts sympathetic vasoconstriction in human skeletal muscle", Journal of Physiology, fol. 586, No. 20, Oct. 15, 2008, pp. 4993-5002.
Hau, W. "Routine Pressure-Derived Fractional Flow Reserve Guidance: From Diagnostic to Everyday Practice", The Journal of Invasive Cardiology, vol. 18, No. 5, May 2006, pp. 240-245.

\* cited by examiner

*Primary Examiner* — Robert A Wax
*Assistant Examiner* — Daniel F Coughlin
(74) *Attorney, Agent, or Firm* — Merchant & Gould P.C.

(57) ABSTRACT

The present invention relates to methods for determining whether blood flow is restricted in a blood vessel of an individual suspected of compromised blood flow in the vessel, the method comprising the steps of delivering UTP, a derivative thereof, or a salt thereof to the vessel, assessing blood flow quantitatively in the vessel by obtaining a value that correlates to blood flow in said vessel, comparing the obtained value with a reference value, and determining whether the individual has compromised blood flow based on the results of the comparison. The invention also provides for methods of diagnosing atherosclerotic and ischemic heart diseases using UTP, a derivative thereof, or a salt thereof, as well as methods for inducing maximal hyperemia for diagnostic purposes.

12 Claims, 8 Drawing Sheets

Diagnostic advantage:
Use of UTP alters clinical decision making more than adenosine

|  | UL/echo | FFR | Myocardial scintigraphy and MPI | MRI/MRA | CT | PET | ABI |
|---|---|---|---|---|---|---|---|
| Coronary artery disease | x | x | x | x | x | x |  |
| Peripheral artery disease | x |  |  |  |  |  | x |
| Aortic stenosis | x |  |  | x |  |  |  |
| Carotid stenosis | x |  |  |  | x |  |  |
| Renal vascular disease | x | x |  | x |  |  |  |

USE OF UTP FOR THE DIAGNOSIS OF STENOSES AND OTHER CONDITIONS OF RESTRICTED BLOOD FLOW

CROSS-REFERENCE TO PRIOR APPLICATION

This application claims the benefit of U.S. Provisional application Ser. No. 61/232,518, filed Aug. 10, 2009 and Ser. No. 61/357, 857 filed Jun. 23, 2010, both of which are incorporated by reference herein in their entirety.

FIELD OF INVENTION

The present invention relates to methods for determining whether blood flow is restricted in a blood vessel of an individual suspected of compromised blood flow in the vessel using UTP, a derivative thereof, or a salt thereof. Also, it relates to compositions containing UTP, a derivative thereof, or a salt thereof for use as a diagnostic agent in the foregoing methods.

BACKGROUND OF INVENTION

The potent and widespread vascular actions of purine nucleotides and nucleosides have long been recognized. Naturally occurring extracellular purine nucleotides and nucleosides exert cardiovascular responses by stimulating various P1 and P2 receptors [1,2]. Adenine nucleotides and nucleosides are used for many diagnostic and treatment purposes in daily clinical practice such as assessment of coronary blood flow [3-8] and as anti-arrhythmic agents. Adenosine non-selectively activates 4 receptor subtypes: A1, A2A, A2B, and A3. Activation of cardiac A2A and A2B adenosine receptors vasodilates the coronary and peripheral arterial beds, increases myocardial blood flow (MBF), and causes sympathoexcitation, but also results in mast cell degranulation and bronchial constriction. Nevertheless, intracoronary and intravenous adenosine are employed in the clinic for assessment of fractional flow reserve (FFR).

Uridine 5-triphosphate (UTP) is also a naturally occurring compound in the circulation and is discharged during acute myocardial infarction. UTP stimulates P2Y2 and P2Y4 receptors, where the first are predominant in the human cardiovascular tree. UTP is highly selective for this receptor.

Previous assumptions underlying the use of UTP in treatment of cardiovascular disease have proved inaccurate in vivo. It was demonstrated in 2004 and 2008 [9, 10], by using local infusion of ATP and UTP, that these two agents were the only registered metabolites capable of opposing sympathetic vasoconstriction and concomitantly increasing blood flow (85% and 60% of maximum in the leg during hard exercise, respectively). However, the present inventor, using systemic infusion of UTP in pigs, has found that UTP can only maximally lower mean arterial pressure by 30% (Example 4), which is substantially less than that achieved by ATP because ATP can produce limitless lowering of blood pressure. Therefore, ATP is more potent than UTP systemically as well as locally in the healthy leg, although both ATP and UTP were shown previously to be equipotent in the peripheral vascular system for the P2Y2 receptor in the arms of humans [11].

The higher potency of ATP compared to UTP in the normal healthy leg was attributed to the degradation of ATP to ADP, AMP, and adenosine. These degradation products, in conjunction with ATP, could contribute to elevate blood flow higher than that achieved by UTP, which does not have any vasoactive degradation products. Thus, a comparison of the relative vasoactive potencies of exogenous nucleotides and adenosine revealed the following rank order: ATP (100)=UTP (100)>>adenosine (5.8)>ADP (2.7)>AMP (1.7), but only for blood flows around 3.5 L min$^{-1}$ [9].

Comparative studies in the human leg of healthy and diabetic patients showed that UTP>>ATP with regard to vasodilation in legs of elderly patients and patients with type 2 diabetes [1,2]. This is clearly in contrast to previous findings, but is more clinically relevant as most cardiac patients are older. Interestingly, the discrepancy in vasoactive potency was not due to an up-regulation of the P2Y2 receptor, suggesting that up-regulation of other ATP-related (but not UTP) vasoconstrictive receptors must be relevant when people are of advanced age and poor general health. However, recent studies have shown that the ability to oppose sympathetic vasoconstriction during exercise is intact in patients with type 2 diabetes, suggesting that previous assumptions of a crucial involvement of the P2Y2 receptor in functional sympatholysis are inaccurate [9]. This conclusion is also supported by another study by the present inventor in pigs where ADP or UTP was infused during myocardial infarction. In that study, UTP increased the infarct area during acute myocardial infarction, whereas ADP diminished it (unpublished results). This suggests a pharmacological cardioprotective effect of ADP, but a detrimental effect of UTP, suggesting that caution must be exercised when using UTP in clinically acute conditions. Therefore, the previous assumptions in patent application WO 2007/065437 relating to the regulation of purinergic receptor activity to modulate vascular tone, particularly for treating hemodynamic conditions by overriding vasoconstriction activity, which could potentially have clinical applications for treatment with UTP agonists or antagonists, is incorrect.

In contrast to the vasodilating properties associated with UTP mentioned above, UTP has also been described to be a potent vasoconstrictor in the coronary circulation. Of particular note are the studies relating to human coronary arteries and bypass vessels [13-15]. In these studies, both UTP and UTPγS induced contractions in coronary arteries and the internal mammary artery in heart transplant patients, suggesting that P2Y2 receptors are important contractile receptors. UTPγS also induced contractions in the saphenous vein. Given that prolonged treatment with UTP has been shown to induce smooth muscle proliferation in vitro, it can be speculated that in case of endothelial dysfunction (such as with coronary artery disease), extracellular nucleotides derived from the blood may reach smooth muscle cells (SMCs), leading to UTP-mediated vasoconstriction of P2Y2 receptors. In human coronary arteries, the P2Y2-subtype has been presumed to play a major role in this speculated constriction [14, 15]. This is also seen in animal studies [16, 17]. In pigs, the P2Y2 receptor is up-regulated in SMCs of in vivo stented coronary arteries to mediate the mitogenic effects of nucleotides [1,8]. Therefore, the P2Y2 receptors are suspected to take part in the pathophysiological genesis of potentially life-threatening vasospasms [15].

Besides being looked at as evoking coronary vasoconstriction of damaged vessels, extracellular nucleotides have also been implicated to play an important role in the development of inflammatory vascular disease [19,20]. Seye et al. showed that UTP, acting at P2Y2 receptors, promoted intimal hyperplasia of collared rabbit carotid arteries [21]. In an animal model, porcine P2Y2 receptors were found to be overexpressed in stented coronaries and to play a distinct mitogenic role there [1,8]. It has thus been accepted that vascular remodeling, facilitated by extracellular nucleotides, is a key step in the genesis of cardiovascular and cerebrovascular disease, potentially culminating in life-threatening states of stroke or heart attack. Therefore, no preceding clinical studies have ever been attempted involving in vivo coronary infusion of UTP in humans, because this compound, for all the above mentioned reasons, was believed to be hazardous to humans.

Angiographic assessment of coronary artery disease (CAD) has guided cardiac therapy for more than 30 years, however even experienced angiographers are unable to reliably assess lesion severity because angiography has significant intra-observer and inter-observer variability and is not a physiological assessment, but merely a visual one. Recent studies, such as the COURAGE trial, have re-emphasized what all current medical guidelines recommend: that for low risk patients, even those experiencing angina, optimal medical therapy should be the initial treatment. For those patients whose disease progresses, or for whom chest pain is not alleviated, revascularization, either through angioplasty and stenting or surgery, should be performed.

The new diagnostic tool fractional Flow Reserve (FFR) helps physicians to decide whether to intervene on a stenosis (i.e., abnormal narrowing of blood vessels) or not. Achievement of maximal hyperemia of coronary microcirculation is a prerequisite for the exact assessment of FFR in order to minimize the effect of microvascular resistance. Thus, the higher the flow, the larger the pressure drop across the stenotic vessel, i.e., the lower the FFR. For accurate FFR measurements, achievement of maximal hyperemia is imperative for minimizing the effect of microvascular resistance. Only at maximal hyperemia is flow and pressure linearly correlated. If there is only suboptimal hyperemia, the FFR index underestimates the functional severity of coronary stenosis. This can lead to injurious outcomes [22]. Therefore, it is crucial for clinical decision making, that the FFR response is accurate, otherwise over- or under-treatment of patients will occur, leading to higher mortality rates and more expensive treatment regimens.

The preferred standard hyperemic agent used today for inducing coronary hyperemia is adenosine. However, adenosine use is associated with side effects even with local infusions. For example, adenosine causes dyspnea and angina in nearly all patients, as well as second-degree AV block in some patients. Adenosine use is also associated with contraindications such as asthma, COPD, angina, hypotension, $2^{nd}$ or $3^{rd}$-degree AV block, and sinus node dysfunction; and the need for abstinence from caffeine in order to get an accurate hyperemic assessment, because caffeine blocks P1 receptors, which are the vasodilatatory receptors the adenine compounds function through [23].

Given the foregoing limitations associated with the use of adenine-related compounds (e.g., adenosine and ATP) as hyperemic agents, more potent hyperemic agents with fewer side effects would be beneficial for diagnosing compromised blood flow in blood vessels.

SUMMARY OF THE INVENTION

The present invention is predicated on the finding of the present inventor that UTP is a better vasodilator than other clinically used vasodilators: adenosine, ATP and NO, which are all equipotent in situations where patients suffer from coronary artery disease. Thus, although UTP may not be used as a therapeutic because it rapidly desensitizes P2Y2 receptors, may cause endothelial cell proliferation which leads to atherosclerosis during prolonged exposure, and has too short a terminal half-life (20 seconds), it can surprisingly be used as an optimal diagnostic agent. This is supported by the evidence (presented in Examples 2 and 3) in humans, who were being evaluated for potential coronary atherosclerosis, showing the much higher potency of UTP: UTP>>ado (=ATP) in terms of vasodilator activity. In this study, it was shown that UTP more effectively lowers FFR than adenosine, allowing for more accurate maximal coronary hyperemia to be achieved. This was the first use of UTP in the context of in vivo coronary circulation. In fact, previous in vitro studies demonstrated that UTP induces vasoconstriction, which would diminish coronary perfusion. Thus, the finding that UTP can induce hyperemia in patients with suspected endothelial dysfunction is surprising.

In contrast to ATP, UTP is highly receptor selective and degraded rapidly (terminal half-life: about 20 sec) in the circulation, rendering an inactive degradation product. Thus, it has no long-term effects. UTP can easily be applied to patients that are in a stable clinical condition or during recurrent angina attacks. Surprisingly, the present inventor also found that UTP is a more potent vasodilator than adenosine and ATP in both peripheral circulation of diabetics and in the coronary circulation of patients with coronary artery disease. Thus, UTP induces maximal hyperemia to a greater extent than both adenosine and ATP. This is an important finding given that maximal hyperemia is important, for example, in the exact measurement of FFR in order to minimize the effect of microvascular resistance.

The advantages of using UTP as a diagnostic therefore include its specific affinity for the P2Y2 receptor, which makes it more receptor selective than other diagnostic agents, UTP (unlike ATP) does not have a degradation product which is vasoactive, and no abstinence from caffeine is required for accurate hyperemic assessment. It reaches the steady state faster and acts rapidly (time to peak, 5 s), it is easy to use, lacks significant side effects, has a terminal half-life of 20 s, has no obvious contraindications, and can be used for patients who have contraindications to the use of adenosine due to, for example, arrhythmia, COPD, or asthma. For the foregoing reasons, UTP is an ideal hyperemic agent for use in diagnosing compromised blood flow in blood vessels.

The inventor has found that UTP, a derivative thereof, or a salt thereof (as further defined below), can be used to determine whether blood flow is restricted in a blood vessel of an individual suspected of compromised blood flow in the vessel, by mimicking the increased blood flow observed during exercise. Accordingly, compromised blood flow can be determined with high accuracy even in individuals at rest. Thus, the method is useful for determining compromised blood flow in any individual, even in individuals who should not or for whom it is undesirable to undergo exercise testing.

The present invention is believed to represent the first diagnostic use of UTP, a derivative thereof, or a salt thereof. Consequently, in one aspect, the invention relates to compositions containing an effective amount of UTP, a derivative thereof or a salt thereof for use as a diagnostic agent in assessing blood flow.

By determining that blood flow is compromised in a blood vessel, preferably an artery of an individual with suspected compromised blood flow, hemodynamic conditions caused by compromised blood flow, particularly but not exclusively stenosis, may be treated more effectively. In particular, stenosis may be recognised before any adverse cardiovascular events, such as myocardial infarction, stroke, and/or death has occurred, providing an opportunity for prophylactic treatment of, for example, renal artery disease, coronary atherosclerosis, ischemic heart disease, or peripheral artery disease (PAD).

Accordingly, in one aspect, the invention relates to a method for determining whether blood flow is restricted in a blood vessel of an individual suspected of compromised blood flow in the vessel, the method comprising:
(a) delivering UTP, a derivative thereof, or a salt thereof to said vessel,
(b) assessing blood flow quantitatively in the vessel by obtaining a value for that indicates or correlates to blood flow in said vessel,
(c) comparing the obtained value with a reference value, and
(d) determining whether the individual has compromised blood flow based on the results of the comparison.

In one embodiment of the above method, the individual is suffering or suspected to be suffering from obesity, hypertension, vasculitis, increased thrombotic risk, hypercholesterolemia, atherosclerosis, diabetic complications, or vascular stenosis. In another embodiment, the individual is suffering from Peripheral Artery Disease (PAD), coronary atherosclerosis, atherosclerosis, renal artery stenosis, or ischemic heart disease.

In another embodiment of the above method, the UTP, derivative thereof, or salt thereof is UTP, UTPγS, MRS2498, uridine 5'-trisphosphate tris salt, uridine 5'-trisphosphate salt dihydrate, uridine 5'-trisphosphate salt solution, uridine 5'-trisphosphate salt hydrate, uridine-$^{13}C_9$, $^{15}N_2$ 5'-trisphosphate sodium salt solution, uridine-$^{15}N_2$ 5'-trisphosphate sodium salt solution, uridine 5'-triphosphate trisodium salt hydrate, uridine-$^{13}C_9$, $^{15}N_2$ 5'-triphosphate sodium salt solution, uridine-$^{15}N_2$ 5'-triphosphate sodium salt solution, 2-diuridine tetraphosphate, thioUTP tetrasodium salt, denufosol tetrasodium, or UTPγS trisodium salt. Infusion of UTP, a derivative thereof, or a salt thereof, can be infused at, for example, from about 50 to about 400 μg of the compound per minute.

In yet another embodiment, the reference value is obtained by measuring blood flow in another similar vessel of said individual. Blood flow is measured, for example, by FFR, CFR, MAP, or APV measurement. In yet another embodiment, delivery occurs by in situ infusion. Delivery can also occur via continuous intravenous infusion, intracoronary infusion, drip infusion, intracoronary bolus injection, guiding catheter, or an IC microcatheter, preferably a guiding catheter or IC microcatheter.

In another aspect, the invention relates to a method for determining whether blood flow is restricted in a blood vessel of an individual suspected of compromised blood flow in the vessel, the method comprising:
(a) delivering UTP, a derivative thereof, or a salt thereof to said vessel,
(b) assessing blood flow quantitatively in the vessel by obtaining a value that correlates to blood flow in said vessel,
(c) comparing the obtained value with a reference value, and
(d) determining whether the individual has compromised blood flow based on whether there is a difference between the obtained value and the reference value indicative of a reduction in blood flow relative to a healthy vessel.

In yet another aspect, the invention relates to a method for determining whether blood flow in a blood vessel of an individual suspected of compromised blood flow in the vessel is restricted, the method comprising:
(a) delivering UTP, a derivative thereof, or a salt thereof to said vessel of an individual suspected of having an atherosclerotic or ischemic disease,
(b) assessing blood flow quantitatively in the vessel by obtaining a value that correlates to blood flow in said vessel,
(c) comparing the obtained value with a reference value, and
(d) determining whether the individual has compromised blood flow based on the results of the comparison.

In yet another aspect, the invention relates to a method for determining blood flow in a blood vessel comprising:
(a) delivering UTP, a derivative thereof, or a salt thereof to an individual suspected of having a vessel with compromised blood flow,
(b) assessing blood flow quantitatively in the vessel by obtaining a value that correlates to blood flow in said vessel,
(c) comparing the obtained value with a reference value, and
(d) determining whether the individual has compromised blood flow based on the results of the comparison.

In a further aspect, the invention relates to a method for diagnosing a disease selected from the group consisting of Peripheral Artery Disease (PAD), coronary atherosclerosis, and ischemic heart disease comprising:
(a) delivering UTP, a derivative thereof, or a salt thereof to an individual suspected of having said disease,
(b) assessing blood flow quantitatively in the vessel by obtaining a value that correlates to blood flow in said vessel,
(c) comparing the obtained value with a reference value, and
(d) determining whether the individual has compromised blood flow based on the results of the comparison.

In yet another aspect, the invention relates to a method for the induction of maximal hyperemia comprising administering to an individual in need thereof UTP, a derivative thereof or a salt thereof. In one embodiment, the hyperemia is coronary hyperemia.

A further aspect of the invention relates to a kit for determining blood flow in a blood vessel comprising: (a) UTP, a derivative thereof, or a salt thereof as an active diagnostic ingredient, and (b) instructions for the use thereof in an individual with suspected compromised blood flow. In one embodiment, the kit further comprises a microcatheter or guiding catheter. In another embodiment, the kit further comprises a physiologically acceptable aqueous carrier, preferably saline. In a further embodiment, the physiologically acceptable aqueous carrier and the active diagnostic ingredient are provided in separate containers.

In another aspect, the invention relates to a diagnostic composition comprising UTP, a derivative thereof, or a salt thereof in a pharmaceutically acceptable aqueous carrier suitable for administration into a human patient, wherein the composition contains from about 50 to about 400 μg/ml of UTP, a derivative thereof, or a salt thereof. In one embodiment, the diagnostic composition containing an effective amount of the diagnostic reagent is delivered to an individual in need thereof in a total volume of about 2 ml to about 10 ml to induce hyperemia, particularly maximal hyperemia.

In yet another aspect, the invention relates to a method for diagnosing renal artery stenosis comprising:
(a) delivering UTP, a derivative thereof, or a salt thereof to an individual suspected of having said disease,
(b) assessing blood flow quantitatively in the vessel by obtaining a value that correlates to blood flow in said vessel,
(c) comparing the obtained value with a reference value, and (d) determining whether the individual has compromised blood flow based on the results of the comparison.

In yet another aspect, the invention relates to a method for screening individuals at risk of developing an atherosclerotic or ischemic disease comprising:
(a) delivering UTP, a derivative thereof, or a salt thereof to the individual,
(b) assessing blood flow quantitatively in the vessel by obtaining a value that correlates to blood flow in said vessel,
(c) comparing the obtained value with a reference value, and
(d) determining whether the individual has compromised blood flow based on the results of the comparison.

In yet another aspect, the invention relates to a method for measuring fractional flow reserve (FFR) comprising:
(a) delivering UTP, a derivative thereof, or a salt thereof to a blood vessel in escalating stepwise doses,
(b) monitoring pressure across the blood vessel until distal pressure reaches a minimum value, wherein the minimum value corresponds to maximal blood flow.

In one embodiment, FFR measures blood flow in a coronary artery. In another embodiment, UTP, a derivative thereof, or a salt thereof is delivered by a delivery device, such as a microcatheter or guiding catheter. In yet another embodiment, UTP, a derivative thereof, or a salt thereof is delivered by intracoronary infusion. In yet a further embodiment, the escalating stepwise doses are 20, 40, 80, 160, 240, 360, and 400 μg/min.

DETAILED DESCRIPTION OF THE INVENTION

DEFINITIONS

Figure 1:
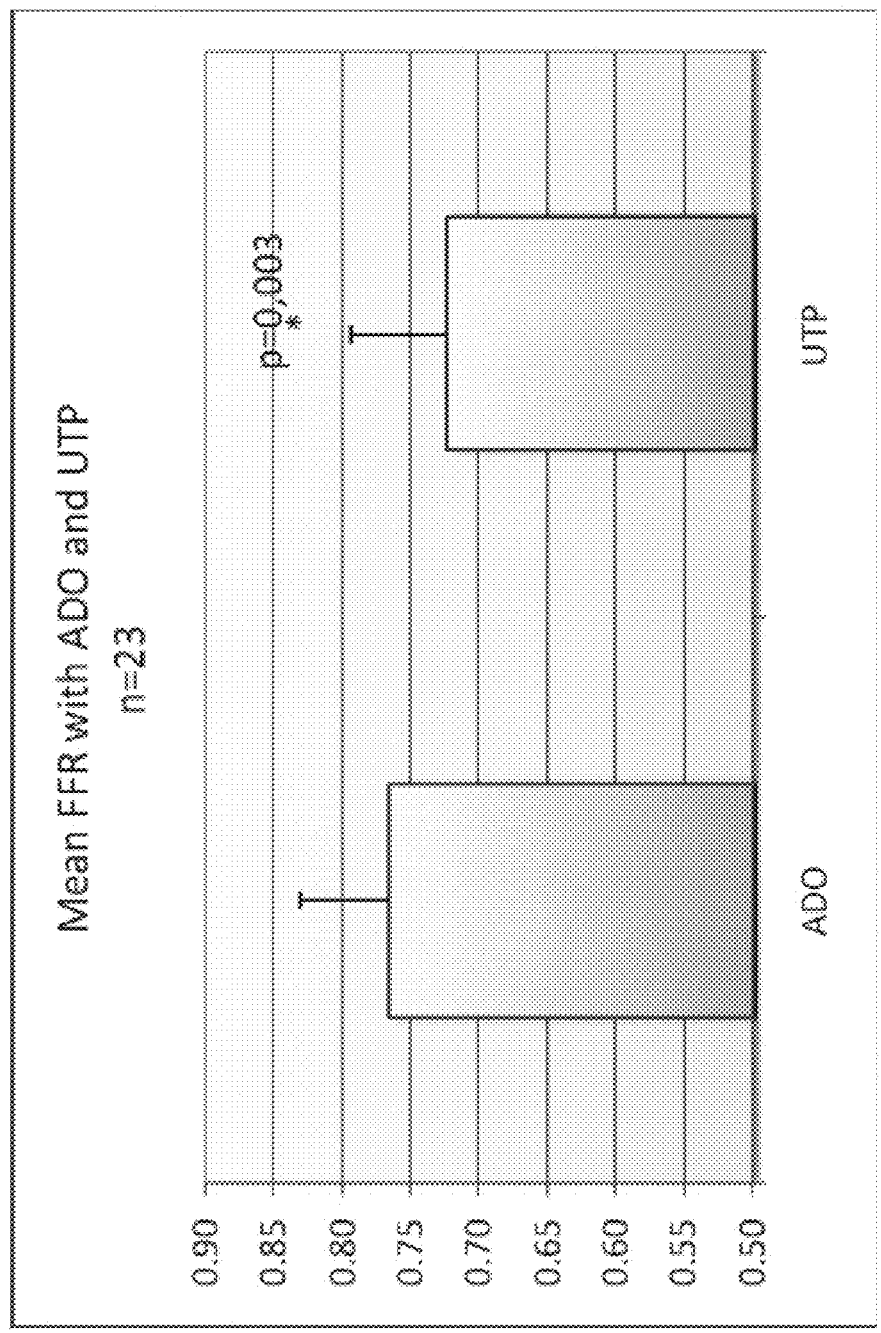
FIG. 1 is a graph showing mean FFR following intracoronary infusion in a guiding catheter of UTP versus adenosine in humans with coronary artery disease. This graph demonstrates that UTP is superior to adenosine for lowering the FFR ratio (p=0.003). The FFR is expressed as the mean of the 23 subjects.
Figure 2:
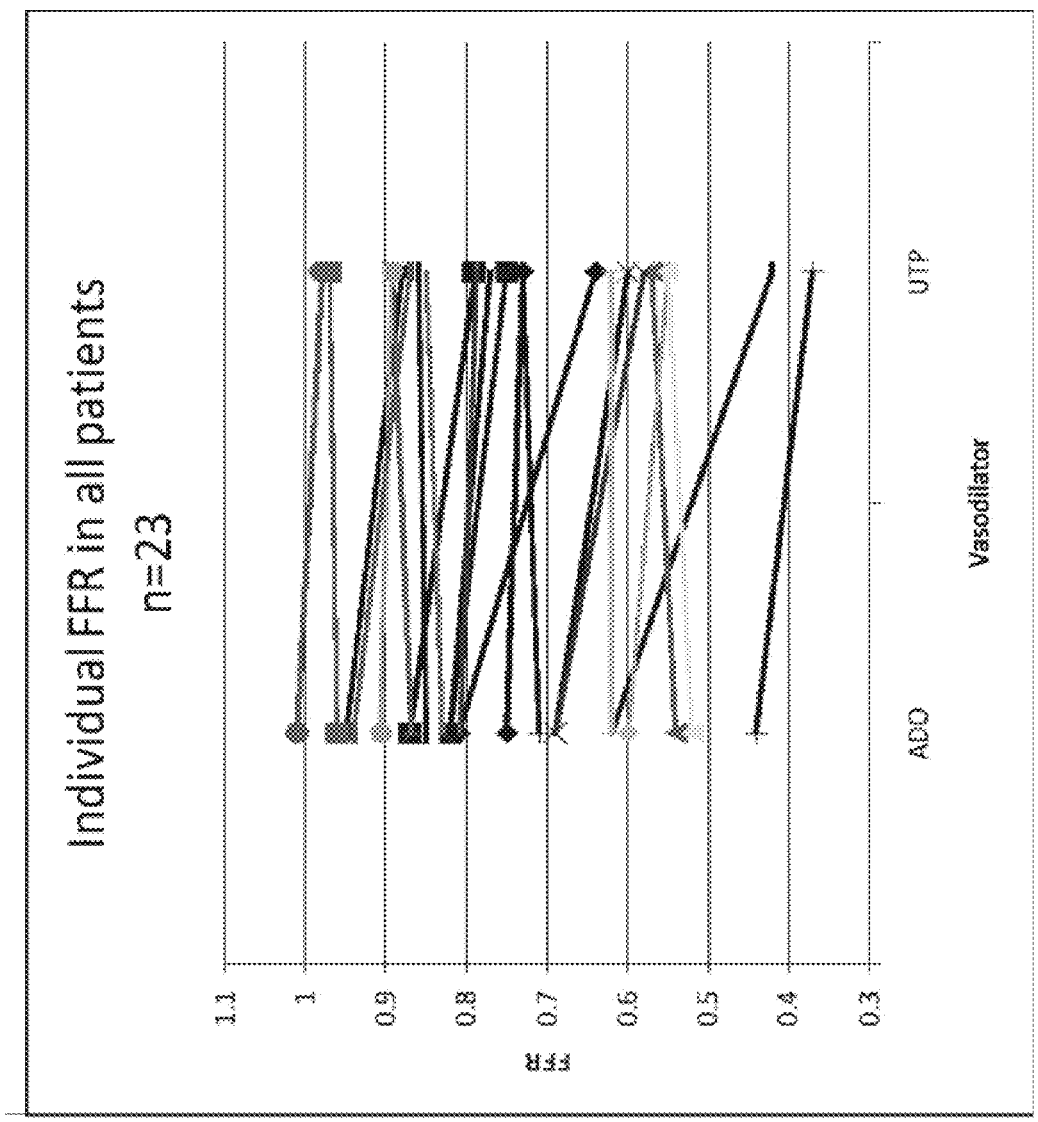
FIG. 2 is a graph showing the patients' individual fractional flow reserve (FFR) following intracoronary infusion of UTP versus adenosine in humans with angiographic stenosis.
Figure 3:
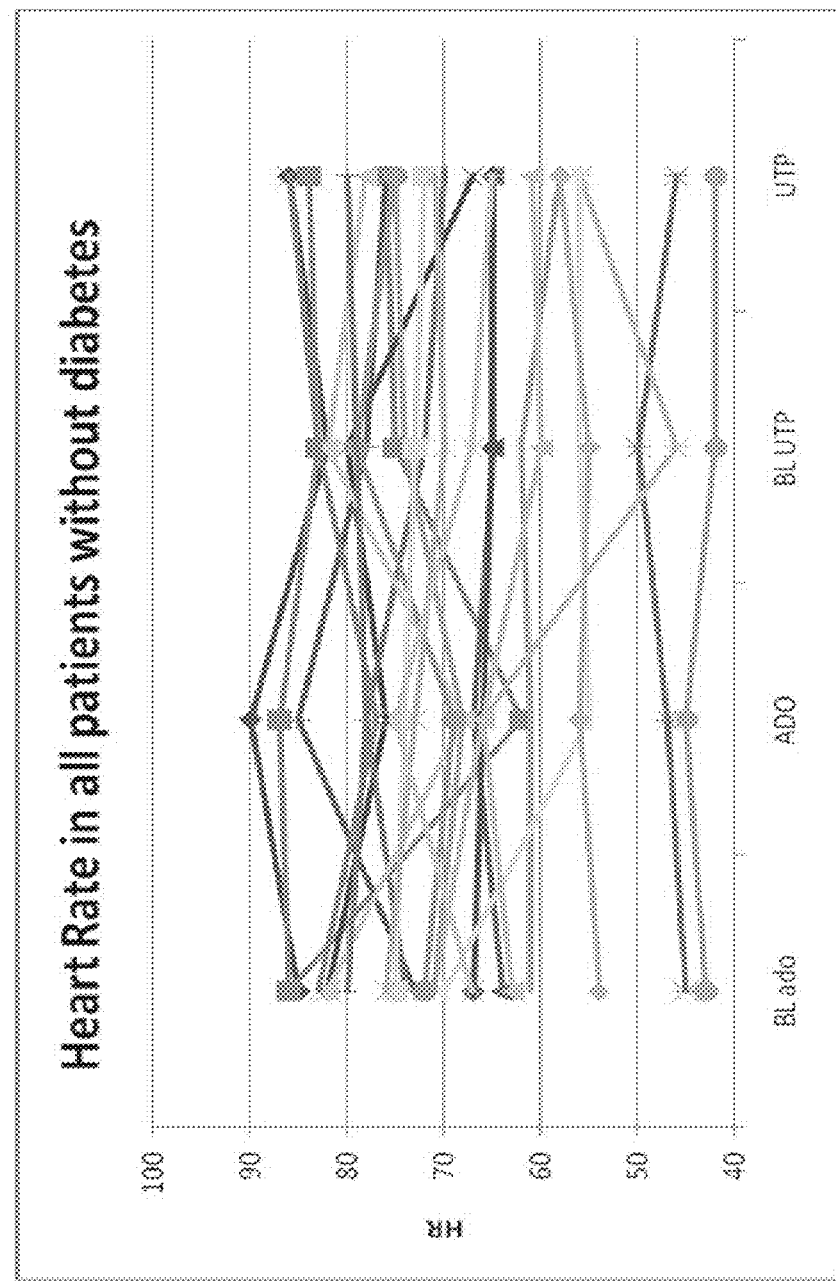
FIG. 3 is a graph showing individual mean heart rate following intracoronary infusion of BL ado, adenosine, BL UTP or UTP.
Figure 4:
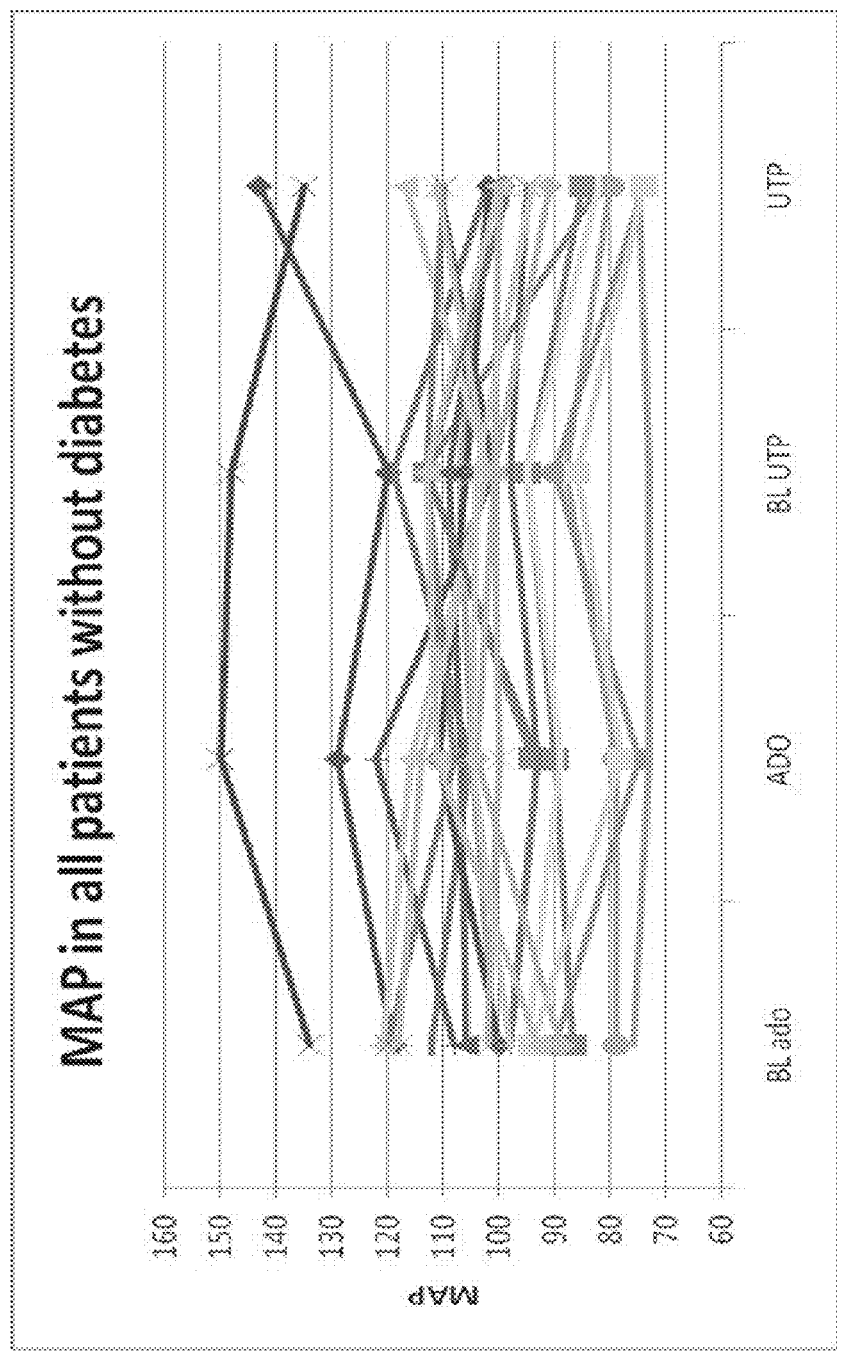
FIG. 4 is a graph showing the patients' individual mean arterial pressure (MAP) and heart rate following intracoronary infusion of baseline (BL) ado, adenosine, BL UTP or UTP.

The term "hypertension", when used herein, refers to high blood pressure. This generally means that the systolic blood pressure is consistently over 140 and/or the diastolic blood pressure is consistently over 90. Hypertension is when either or both of the systolic blood pressure and the diastolic blood pressure are too high.

"Ischemic heart disease" or myocardial ischemia as used herein refers to a disease characterized by reduced blood supply to the heart muscle, usually due to coronary artery disease (atherosclerosis of the coronary arteries).

A "stenosis" as used herein, is be defined as an abnormal narrowing in a blood vessel or other tubular organ or structure.

"Individual" or "subject" as used herein is intended to mean any mammal, including a human, veterinary animal, (such as a farm animal, a domestic animal), or laboratory animal (such as a rodent or a primate).

"P2Y2 receptor" as used herein is intended to mean a G protein-coupled extracellular nucleotide receptor associated with a PI signalling pathway, which may be activated for example by extracellular nucleotides.

"Normal blood flow" as used herein is intended to mean blood flow that is uncompromised by, for example, a stenosis or a blood clot. A standard for normal blood flow may for example be developed by measuring the blood flow in at least 20 healthy individuals with no suspected illnesses and determining the average.

"Compromised blood flow" as used herein is intended to mean any abnormality in which blood flow through a vessel is lower than normal blood flow due to a constriction, or mechanical obstruction or inflexibility in the vessel wall, such as stenosis. Compromised blood flow may be assessed by many parameters including but not limited to a drop in blood pressure and may be measured in arteries and veins as well as in functional tissue.

"Hyperemia" as used herein is intended to mean the increase of blood flow to different tissues in the body.

"Maximal hyperemia" as used herein is intended to mean maximal increase in blood flow, which can be induced by the administration of modulators of the P2Y2 receptor, which according to the present invention is UTP, derivatives thereof, or salts thereof as further defined below. This can be measured, inter alia, by measuring the pressure difference between the proximal end and the distal end of a blood vessel suspected of compromised blood flow. When using this methodology, maximal hyperemia is considered reached when upon further supply of UTP, a UTP derivative, or a salt thereof, the distal pressure does not change.

"Ankle-brachial index" as used herein is intended to mean the ratio of the blood pressure in the lower legs to the blood pressure in the arms "Derivative" as used herein is intended to refer to substitution(s) or modification(s) of any group or groups on UTP, not limited to those disclosed herein, that results in a compound that activates the P2Y2 receptor to a degree in which the ratio of the EC50 for stimulation of the human P2Y2 receptor divided by the EC50 for stimulation of the human P2X1 receptor is higher, such as at least 2 fold higher, than the corresponding ratio for ATP. Examples of such derivatives include, but not limited to, UTPγS, MRS2498, uridine 5'-trisphosphate tris salt, uridine 5'-trisphosphate salt dihydrate, uridine 5'-trisphosphate salt solution, uridine 5'-trisphosphate salt hydrate, uridine-$^{13}C_9$, $^{15}N_2$ 5'-trisphosphate sodium salt solution, uridine-$^{15}N_2$ 5'-trisphosphate sodium salt solution, uridine 5'-triphosphate trisodium salt hydrate, uridine-$^{13}C_9$, $^{15}N_2$ 5'-triphosphate sodium salt solution, uridine-$^{15}N_2$ 5'-triphosphate sodium salt solution, 2-diuridine tetraphosphate, thioUTP tetrasodium salt, denufosol tetrasodium, or UTPγS trisodium salt.

The term "significant difference" is used herein to mean that the difference in a measured value (e.g., in amount of blood flow determined in a subject) and a reference value is indicative of restricted blood flow.

The term "reference value" may have different meanings depending on context. For example, in some cases, a "reference value" refers to the range of normal values for blood flow (which may be assessed directly or indirectly by measuring another variable that correlates to blood flow). Alternatively, a "reference value" may represent the value of blood flow associated with an abnormal condition. For example, when fractional flow reserve is used to assess blood flow, the measured value is pressure differential between the distal end of a stenotic blood vessel segment under conditions of maximal hyperemia and the reference value is the corresponding pressure differential under similarly hyperemic conditions in the same vessel without stenosis. The ratio of the two provides the comparison. If the ratio is 1 (and blood is actually flowing through the vessel) there is no stenosis. It is also possible, however, for a reference value to be a value indicating abnormality (usually a threshold value), in which case, the comparison would show whether the measured value has a certain relationship to the reference value (e.g., higher or lower than the threshold abnormality value) The connotation of "reference value" as used in a specific context will be apparent to one of ordinary skill in the art.

"About" as used herein is intended to mean within a statistically meaningful range of a value. Such a range can be within an order of magnitude, preferably within 50%, more preferably within 20%, more preferably still within 10%, and even more preferably within 5% of a given value or range. The allowable variation encompassed by the term "about" depends on the particular context under study, and can be readily appreciated by one of ordinary skill in the art. For example, "about" may reflect experimental error or experimental variation in measurement or interpatient differences. As a specific example, "about 20 seconds" when referring to terminal half-life of UTP would encompass inter-patient differences of up to 10 to 60 seconds depending upon ectonucleotidase activity in a given patient.

"Delivery" as used herein is intended to include any administration that causes an effective concentration of the administered substance to be in contact with the vessel being assessed. Included without limitation are in situ administration to the vessel, for example, infusion using a guiding, FFR/thermodilution catheter (PressureWire™ Certus (St. Jude Medical, Inc.)) which enables simultaneous measurement of thermo-dilution flow (via infusion of saline) and concurrent gathering of FFR and CFR (coronary flow reserve), or a microinfusion catheter, or systemic administration to the bloodstream via an intravenous catheter.

"At risk" as used herein is intended to refer to individuals with a genetic predisposition to developing a vascular disease or individuals who have undergone a procedure to treat a vascular disease. A genetic predisposition may, for example, be a mutation in a gene required for normal organ function. Individuals who have undergone a procedure to treat a disease may be at risk for redeveloping the disease or condition, for example, restenosis.

"Fractional flow reserve" or "FFR" as used herein is intended to mean the ratio of absolute distal pressure to proximal pressure at maximal hyperemia. FFR is defined as an index described as the ratio of the hyperemic flow in a stenotic artery to the hyperemic flow in the same artery if there was no stenosis present.

EMBODIMENTS

The methods described herein are useful in determining compromised blood flow in an individual with suspected compromised blood flow. Such methods mimic the increased blood flow that occurs during exercise and are thus particularly useful in patients who cannot undertake exercise or for whom it is less desirable to undertake exercise.

The present invention relates to a method for determining whether blood flow is restricted in a blood vessel of an individual suspected of compromised blood flow in the vessel, the method comprising the steps of: (a) delivering UTP, a derivative thereof, or a salt thereof to said vessel, (b) assessing blood flow quantitatively in the vessel by obtaining a value that indicates or correlates to blood flow in said vessel, (c) comparing the obtained value with a reference value, and (d) whether the individual has compromised blood flow based on the results of the comparison.

The methods of the invention may be used to determine a suspected compromised blood flow in any blood vessel in the body. Thus, UTP, a derivative thereof, or a salt thereof, can be delivered to any blood vessel in the body. While the vessel is preferably an artery, it is also possible to determine compromised blood flow in a vein. Compromised blood flow in a vein may, for example, be caused by a stenosis in a vein, such as a stenosis in a graft from a bypass surgery. Within the scope of the present invention is included measuring the blood flow across any artery. In preferred embodiments, blood flow is measured in a coronary artery, such as the main stem artery, right coronary artery, left coronary artery, or any other appropriate coronary artery. In other equally preferred embodiments, blood flow is measured in the any of the common iliac arteries, including, but not limited to, the femoral artery, iliac artery, or popliteal artery.

By delivering UTP, a derivative thereof, or a salt thereof, in accordance with the method of the invention, hemodynamic conditions can be diagnosed more effectively, with reduced or eliminated side-effects, thereby allowing the physician to determine the extent of abnormality, if any, more accurately, and make a more informed choice as to the course of treatment, if any, to be pursued.

For instance, atherosclerosis is a condition in which an artery wall thickens as the result of a buildup of fatty materials such as cholesterol. Atherosclerosis may give rise to various symptoms (e.g., claudication, angina pectoris), and depending on the symptoms, atherosclerosis may be referred to as, for example, PAD (peripheral artery disease), coronary atherosclerosis, or TCI (transient coronary ischemia).

Using the methods described herein, it is possible to determine compromised blood flow, which may be an indication that an individual is suffering from an atherosclerotic disease. The atherosclerotic disease may be any atherosclerotic disease, for example, coronary artery disease (CAD), Peripheral Artery Disease (PAD), renal artery disease, vascular stenosis, aortic stenosis, renal artery stenosis, and coronary atherosclerosis. In a particular embodiment, the disease is CAD.

Coronary artery disease and its clinical manifestations, such as myocardial infarction, are heritable traits. While methods such as percutaneous coronary intervention (PCI) can successfully treat coronary artery disease, there still remains a need for effective diagnostic screening methods. Such diagnostic screening methods are important not only in those afflicted with the disease, but also to screen those at risk for developing the disease due to, for example, restenosis or a genetic predisposition to coronary artery disease. Such screening methods can be, but are not limited to, FFR, CFR, MAP, APV measurements. Thus, methods of the present invention can be applied to screen at-risk patients. These screening methods need not be limited only to at-risk individuals, but can, for example, be incorporated into routine heath checkups and performed on a regular basis.

Coronary artery disease and its clinical manifestations, including myocardial infarction, are heritable traits, consistent with a role for inherited DNA sequence variation in conferring risk for disease. There are many modifiable risk factors for heart disease, such as smoking or exposure to environmental tobacco smoke, obesity, sedentary lifestyle, diabetes, high cholesterol or abnormal blood lipids, and hypertension. There are also non-modifiable risk factors, such as male sex, age >50 years, and a family history of heart disease. Many biological markers, including elevated levels of homocysteine, are associated with an increased risk for atherosclerosis and it has been recognized that some people have a common defective genetic variant (called methylenetetrahydrofolate reductase, "MTHFR") that leads to elevated levels of homocysteine. Furthermore, certain genes are associated with increased risk of CAD. One example is a common polymorphism located on chromosome 9p21.3. Moreover, many loci, including 9p21, are located in intergenic segments and elicit the phenotype by novel mechanisms which need further elucidation.

Methods of the invention can also be used to determine compromised blood flow in an individual who is suffering or suspected of suffering from atherosclerosis, obesity, hypertension, vasculitis, increased thrombotic risk, hypercholesterolemia, diabetic complications, or vascular stenosis. Compromised blood flow may also be an indication that an individual is suffering from ischemic heart disease. Ischemic or ischemic heart disease (IHD), or myocardial ischemia, is a disease characterized by reduced blood supply to the heart muscle, usually due to coronary artery disease (atherosclerosis of the coronary arteries).

The methods described herein are also useful for the determination of compromised blood flow, which may also be an indication that an individual has a blood clot. A blood clot or a thrombus is the inappropriate activation of the hemostatic process in an uninjured or slightly injured vessel. A thrombus in a large blood vessel (mural thrombus) will decrease blood flow through that vessel. In a small blood vessel (occlusive thrombus), blood flow may be completely cut-off, resulting in death of tissue supplied by that vessel. Thus, in one embodiment of the invention, the suspected compromised blood flow is caused by stenosis, particularly a coronary stenosis or any stenosis in the iliacs, such as femoral arterial stenosis.

PAD is an atherosclerotic disease that leads to a narrowing of the arteries, particularly in the legs. This narrowing (i.e., stenosis) limits the amount of blood able to pass through the arteries, resulting in claudication. PAD is associated with significant morbidity and mortality. Medical therapy, including risk factor modification and antiplatelet medications, reduces cardiovascular morbidity and mortality rates in patients with PAD. This is why availability of safe, effective and improved diagnostics is crucial.

Patients who cannot perform treadmill exercises are presently tested with active pedal plantar flexion or with inflation of a thigh cuff well above systolic pressure, in an attempt to produce "reactive" hyperemia. Unfortunately, many patients do not tolerate the discomfort associated with this degree and duration of cuff inflation, so this method is rarely performed. Therefore, pharmacological diagnostics methods which selectively increase blood flow to the legs at rest and simulate exercise are desirable alternatives. UTP will, when infused systemically (i.v.), (Example 3), induce increases in cardiac output by increasing heart rate (thus simulating exercise), thereby increasing blood flow to the legs. This makes a stenotic lesion easily detectable by methods for assessing blood flow. Doppler ultrasound, ankle brachial index monitoring, and the like, as described herein. Thus, in one embodiment, UTP, a derivative thereof, or a salt thereof, is contemplated for use in determining whether blood flow is restricted in a blood vessel of an individual suffering or suspected of suffering from PAD.

Renal artery stenosis often leads to drug resistant hypertension. Determination of renal arterial stenosis severity can be assessed in a similar manner as coronary artery stenosis by use of the pressure gradient and vessel diameter in the kidney [24]. Renal arteries can be examined bilaterally using the same femoral approach as coronary FFR, and bilateral selective renal arteriograms can be obtained. By utilizing the vasoactive effects of UTP to induce renal hyperemia, a pressure gradient across the renal arteries can be assessed. While adenosine lowers glomerular filtration rate by constricting afferent arterioles and causes dose-dependent renal vasoconstriction [25], UTP induces renal vasodilatation [26]. Therefore, a combined catheter with pressure and UTP infusion ensures local infusion and avoids systemic spill over. Thus, UTP, a derivative thereof, or a salt thereof, can be used in conjunction with the methods described herein to detect the presence of renal stenosis.

UTP, a derivative thereof, or a salt thereof, can also be used for the noninvasive testing for renal artery stenosis by socalled Duplex scanning, which is a non-invasive ultrasound method that is both sensitive and specific for detecting stenotic lesions and the severity of the stenosis. They can then be categorized and UTPs hemodynamic significance or renal blood flow can be evaluated. Noninvasive diagnostic technologies continue to advance, and as new methods are validated, the need for renal arteriography may lessen. UTP infusion during duplex scan could be such a diagnostic test.

Stenosis can have many causes. A stenosis within the scope of the present invention may have any underlying cause including, but not limited to, stenosis caused by atherosclerosis, ischemia, infection, neoplasm, inflammation, or smoking. Thus, in a particular embodiment, the methods described herein may be used for the determination of compromised blood flow, which may be an indication that an individual has a stenosis.

Methods described herein can also be applied to the detection of hyperproliferative vascular diseases resulting from mechanical injury, for example, that arising from the use of stents, catheters, and the like.

UTP, UTP Derivatives, and UTP Salts

UTP is available from commercial sources (e.g., Sigma Aldrich (St. Louis, Mo.), Trilink Biotechnologies, Inc. (San Diego, Calif.), Axxora (Nottingham, England and Loerrach, Germany), Torcis Bioscience (Ellisville, Mo.), Inspire Pharmaceuticals, Inc. (Durham N.C.)). Nucleoside phosphates are also commercially available (Sigma Aldrich) or can be made from the corresponding nucleosides by methods known to those skilled in the art. Likewise, where nucleosides are not commercially available, they can be made by modifying readily available nucleosides, or by synthesis from heterocyclic and carbohydrate precursors by methods known to those skilled in the art.

UTP, a derivative thereof, or a salt thereof, used in the invention is capable of stimulating the human P2Y2 receptor to a degree in which the ratio of the EC50 for stimulation of the human P2Y2 receptor divided by the EC50 for stimulation of the human P2X1 receptor is higher, such as at least 2 fold higher, than the corresponding ratio for ATP.

Without being bound a specific theory, it is believed that any UTP-related compound that has such a higher ratio as compared to ATP provide the same advantages as ATP in that they can increase blood flow and override increases in muscle sympathetic vasoconstrictor activity, but do not have, or have to a lesser degree, the disadvantages of ATP, i.e., the activation of purinergic P2X receptors, which results in vasoconstriction and risk of hypertension.

The formula for UTP and certain derivatives is provided below.

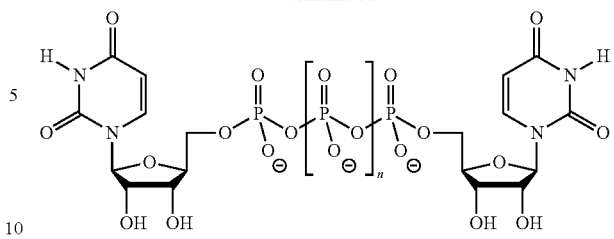

12 n = 1 Up$_3$U
13 n = 2 Up$_4$U
14 n = 3 Up$_5$U
15 n = 6 Up$_6$U

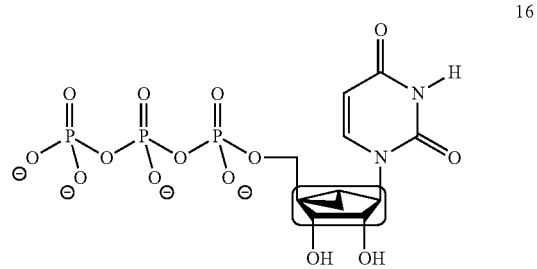

(N)-Methanocarba-UTP

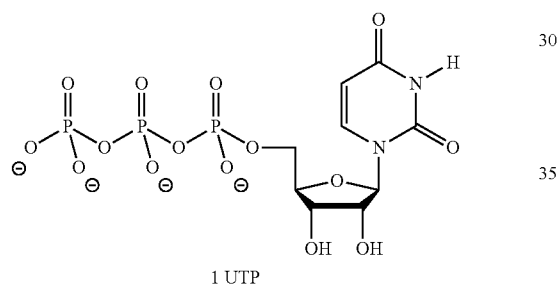

1 UTP

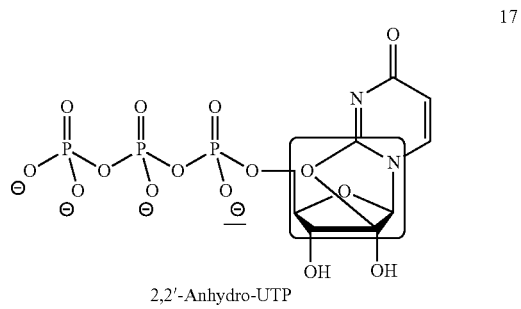

2,2'-Anhydro-UTP

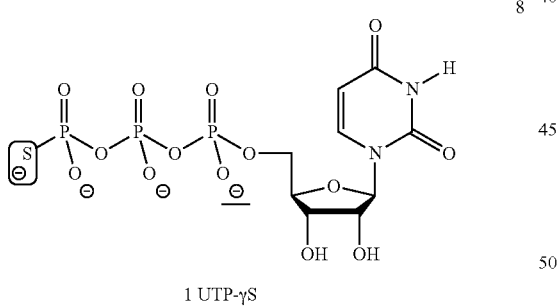

1 UTP-γS

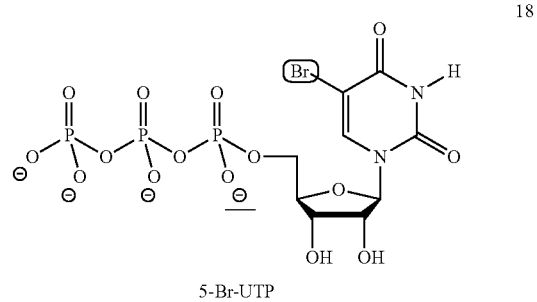

5-Br-UTP

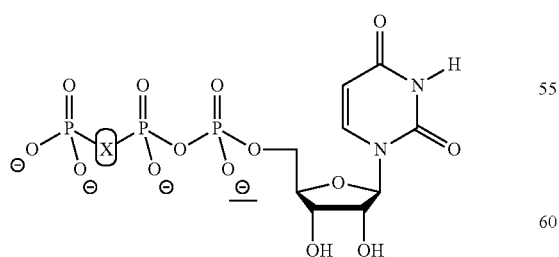

1 X = O      UTP
9 X = NH     UppNHp (β,γ-Imido-UTP)
10 X = CH$_2$   UppCH$_2$p (β,γ-Methylene-UTP)
11 X = CF$_2$   UppCF$_2$p (β,γ-Dichloromethylene-UTP)

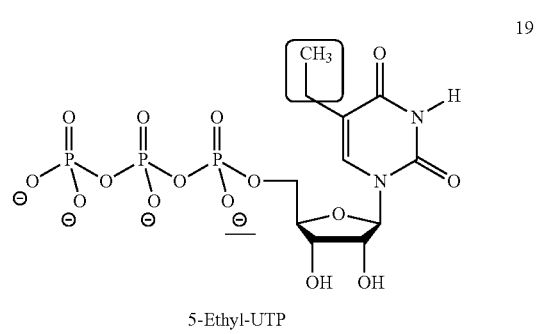

5-Ethyl-UTP

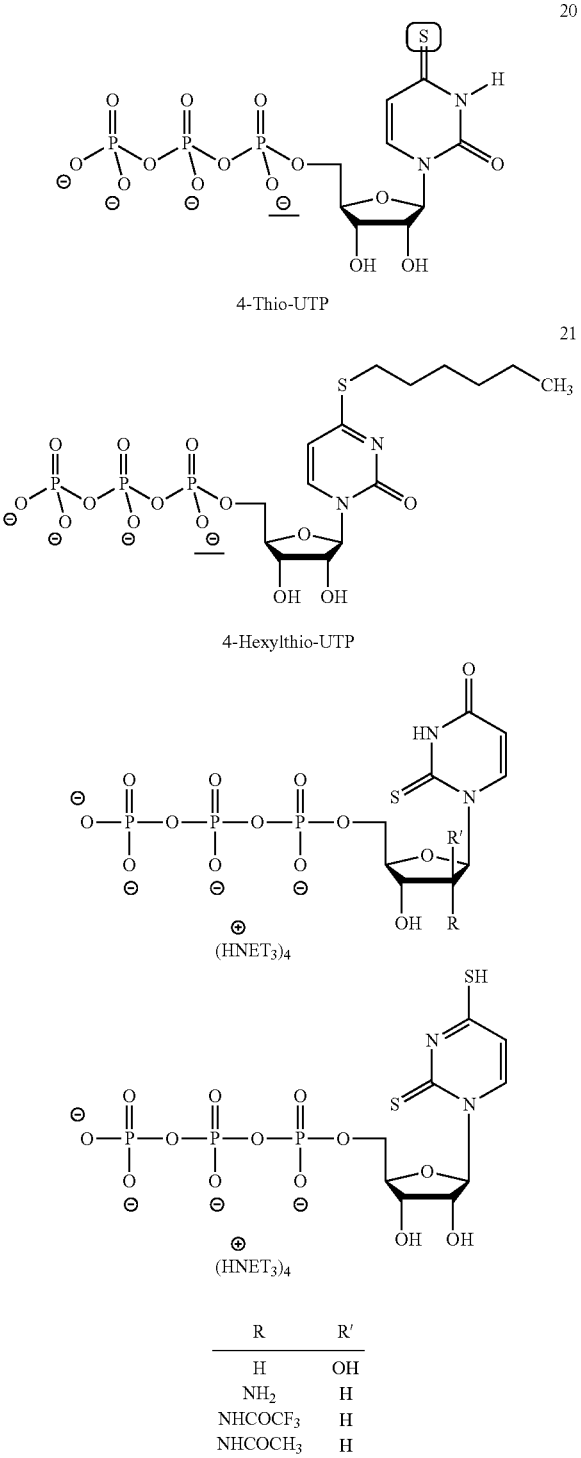

| R | R' |
|---|---|
| H | OH |
| NH₂ | H |
| NHCOCF₃ | H |
| NHCOCH₃ | H |

A UTP derivative has a modification or substitution of one or more residues of UTP. Preferably, a UTP derivative is a compound comprising UTP, wherein one or more —H are exchanged for another group, such as one or more —H groups of the ribose moiety or one or more —H groups of the pyrimidine moiety. Preferably said —H is exchanged with another group selected from the group consisting of lower alkyl, lower alkenyl, lower alkoxy, lower alcohol, —OH, lower amines, —NH₂ and halogen. Lower in this sense means $C_{1-6}$, preferably $C_{1-3}$, and thus by way of example a lower amine, may for example be $C_{1-6}$-alkyl-NH₂ or a $C_{1-6}$-alkenyl-NH₂. Examples of UTP derivatives include, but are not limited to, 5-substituted UTP-derivatives, for example 5, alkyl substitutions, and C'-alkyl UTP derivatives, for example, containing alkyl groups in different positions of the ribose moiety. Alkyl substitutions include, but are not limited to, methyl, ethyl, proplyl, pentyl, hexyl, heptyl, octyl, nonyl, decyl, undecyl and dodecyl substitutions [27].

Other substitutions include, but are not limited to, methylene, propylene, amino, sugar, any halogen and propenyl substitutions at any uridine residue. A UTP derivative may have one or more modifications and/or substitutions. For example, a UTP derivative may have one modification and/or substitution, such as two modifications and/or substitutions, for example three modifications and/or substitutions or four modifications and/or substitutions.

Other ribose modifications include, but are not limited to, 2'-deoxy, 2'-deoxy-2'-methoxy, 3'-deoxy-3'-methoxy, 2'-amino-2'-deoxy, 2'-azido-2'-deoxy, 2'-deoxy-2'-fluoro, arabino, and 2'-deoxy-arabino-2'-fluoro. Some specific uridine modifications include, but are not limited to, 5-bromo, 5-iodo, 5-methyl, 2-thio, 4-thio, 6-aza, and 3-methyl.

Other specific UTP derivatives include 5-(3-amino-1-propenyl)-2'-deoxyuridine-5'-triphosphate, tetrasodium 5-(3-amino-1-propenyl)-2'-deoxyuradine-5'-triphosphate, tetrapotassium 5-(3-amino-1-propenyl)-2'-deoxyuridine-5'-triphosphate, tetraammonium 5-(3-amino-1-propenyl)-2'-uridine-5'-triphosphate, tetrasodium 5-(3-amino-1-propenyl)-2'-uridine-5'-triphosphate, tetrapotassium 5-(3-amino-1-propenyl)-2'-uridine-5'-triphosphate, UTPγS, β,γ-Imido-UTP, β,γ-Methylene-UTP, β,γ-Difluoromethylene-UTP, Up₃U, Up₄U, (N)Methanocarba-UTP, 2,2'-AnhydroUTP, 5-BrUTP, 5-Ethyl-UTP, 4-Thio-UTP and, 4-Hexylthio-UTP, (RP)-α-thio-UTP, (SP)-α-thio-UTP, 2'-Deoxy-(RP)-α-thio-triphosphate, 9, α,β-methylene-UDP, Up4-phenyl ester, Up4-[1]glucose, and (P1-(uridine 5')-P4-(2'-deoxycytidine 5')tetraphosphate).

In particular embodiments, the compound capable of stimulating the P2Y2 receptor is UTPγS, MRS2498, Uridine 5'-trisphosphate tris salt, Uridine 5'-trisphosphate salt dihydrate, Uridine 5'-trisphosphate salt solution, Uridine 5'-trisphosphate salt hydrate, Uridine-$^{13}C_9$, $^{15}N_2$ 5'-trisphosphate sodium salt solution, Uridine-$^{15}N_2$ 5'-trisphosphate sodium salt solution, Uridine 5'-triphosphate trisodium salt hydrate, Uridine-$^{13}C_9$, $^{15}N_2$ 5'-triphosphate sodium salt solution, Uridine-$^{15}N_2$ 5'-triphosphate sodium salt solution, 2-diuridine tetraphosphate, ThioUTP tetrasodium salt, denufosol tetrasodium, or UTPγS trisodium salt.

In other particular embodiments. the compound used in the invention is a compound of the general formula (I):

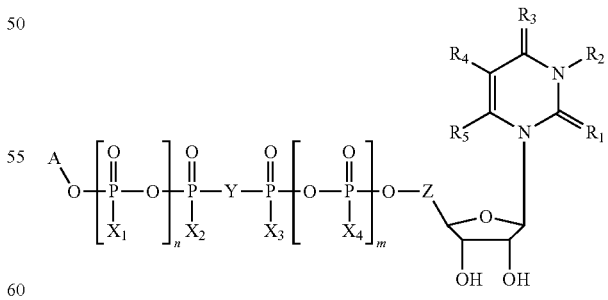

wherein,
R1 is O, S, hydroxyl, mercapto, amino or cyano, R2 is H, Br, nothing, acyl, $C_{1-6}$ alkyl or sulphonate, R3 is O, S, hydroxyl, mercapto or amino, R4 is H, hydroxyl, methyl, cyano, nitro, halogen such as Br, R5 is H or Br
$X_1$, $X_2$, $X_3$ and $X_4$ are independently O" or S", Y is O, imido, methylene or dihalomethylene, such as difluoromethylene, Z is $CH_2$, n and m are independently 0 or 1, and n+m is 0, 1 or 2, A is H or ribose, linked at the 5 position with a pyrimidine or purine residue or pyrimidine or purine derivative selected from the group of uracil, cytosine, guanine, adenine, xanthine, hypoxanthine, linked through the 1 or 9 position, respectively or ribose linked at the 5 position with a pyrimidine residue having formula II

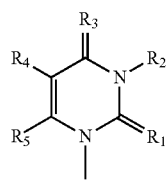

formula (II)

wherein the denoted R groups are as listed above or ribose lined at the 5 position with a purine residue having formula (III)

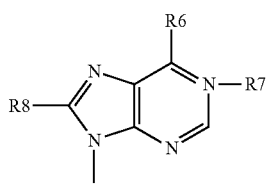

formula (III)

wherein R6 is NH2, while R7 is nothing and there is a double bond between N1 and C6 (adenine) or wherein R6 is NH2 and R7 is O and there is a double bound between N1 and C6 (adenine-1-oxide) or wherein R6 and R7 together form a ring of —NCH═CH— from N6 to N1 with a double bound between N-6 and C6 (1, $N^6$-ethenoadenine), In a further embodiment, the compound used is $P^1$-(uridine 5')—$P^4$-(2'-deoxycytidine 5')tetraphosphate or a salt thereof, such as a tetrasodium salt (INS37217).

In yet further embodiments, the compound capable of stimulating the P2Y2 receptor is one of the compounds described in U.S. Pat. No. 5,292,498 (paragraph 2, line 1 to line 32) and U.S. Pat. No. 5,789,391 (paragraph 2, line 40 to paragraph 3, line 55). In yet another embodiment, the compound used is a P2Y2 agonist described in U.S. Pat. No. 5,837,861, such as P1,P4-Di(uridine 5'-P2,P3-methylene tetraphosphate), P1,P4-Di(uridine 5'-P2,P3-difluoromethylenetetraphosphate), P1.P4-Di(uridine 5'-P2,P3-imidotetraphosphate), P1,P4-Di(4-thioruridine 5'-tetraphosphate), P1,P5-Di (uridine 5'-pentaphosphate), and P1,P4-Di(3,$N^4$-ethenocytidine 5'-tetraphosphate).

UTP, a derivative thereof, or a salt thereof, may be formulated as a free base or salt. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Preferred salts of UTP, a derivative thereof, or a salt thereof, are alkali salts or alkali earth salts, such as sodium salts, potassium salts, calcium salts and magnesium salts. Other preferred salts include, but are not limited, to tris salts, hydrates and dihydrates. The UTP salt may comprise one or more of the above mentioned salts on any UTP residue, such as disalts, trisalts and tetrasalts, for example disodium salts, dipotassium salts, dicalcium salts and dimagnesium salts, as well as trisodium salts, tripotassium salts, tricalcium salts and trimagnesium salts and tetrasodium salts, tetrapotassium salts, tetracalcium salts and tetramagnesium salts. The UTP salts may be substituted on any UTP residue, preferably the salts are 5' or C' substituted.

Formulations and Modes of Administration

UTP, a derivative thereof, or a salt thereof may be delivered in any suitable way known in the art. Preferred modes of delivery include parenteral, intravenous, intra-arterial, in situ infusion, and the like.

UTP, a derivative thereof or a salt thereof may be formulated for parenteral administration (e.g., by injection, for example bolus injection or continuous infusion) and may be presented in unit dose form in ampoules, pre-filled syringes, small volume infusion or in multi-dose containers with an added preservative. A diagnostic composition for parenteral administration may include sterile aqueous and non-aqueous injectable solutions, dispersions, suspensions or emulsions in oily or aqueous vehicles, for example solutions in aqueous polyethylene glycol, as well as sterile powders or lyophilisates to be reconstituted in sterile injectable solutions or dispersions prior to use.

UTP, a derivative thereof, or a salt thereof, may be in powder form, obtained by aseptic isolation of sterile solid or by lyophilisation from solution for constitution before use with a suitable vehicle, e.g., sterile, pyrogen-free water. Aqueous solutions should be suitably buffered if necessary, and the liquid diluent first rendered isotonic (i.e., to an osmolarity of about 300 mOsm) with sufficient saline or glucose. Solubility of UTP, a derivative thereof, or a salt thereof increases by warming and lowering the pH of the aqueous solution. The resulting aqueous solution can be sterilized by filtration. The aqueous solutions can also be heated to a sterilization temperature, e.g., 99° C. for 10 min at physiological pH values, e.g., in order to inactivate enzymes such as ecto-nucleotidases and ectophosphatases, without degradation of the nucleotides. The aqueous solutions are particularly suitable for in situ infusion, and intravenous, intramuscular, subcutaneous and intraperitoneal delivery. The sterile aqueous media employed are all readily available by standard techniques known to those skilled in the art. The reagent and vehicle, of course, can be provided in ready-to-use (pre-sterilized) form after reconstitution at the use point.

Solutions of compounds or pharmaceutically acceptable salts thereof can be prepared in water or saline, and optionally mixed with a nontoxic surfactant. Compositions for in situ infusion, or intravenous or intra-arterial delivery may include sterile aqueous solutions that may also contain buffers, liposomes, diluents and other suitable additives.

The compounds of the present invention may be administered parenterally in a sterile medium. The compound, depending on the vehicle and concentration used, can either be suspended or dissolved in the vehicle. Advantageously, adjuvants such as local anesthetics, preservatives and buffering agents can be dissolved in the vehicle including UTP degradation enzyme blockers. The sterile injectable preparation may be a sterile injectable solution or suspension in a non-toxic parentally acceptable diluents or solvent. Among the acceptable vehicles and solvents that may be employed are physiological saline, sterile water or Ringer's solution.

The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The dosage forms suitable for injection or infusion can include sterile aqueous solutions comprising the active ingredient. In all cases, the ultimate dosage form must be sterile, fluid and stable under the conditions of manufacture and storage.

Sterile injectable solutions can be prepared by incorporating the compound(s) or pharmaceutically acceptable salt(s) thereof in the required amount in the appropriate solvent with various of the other ingredients enumerated above, as required, followed by filter sterilization.

In preferred embodiments, UTP, a derivative thereof or a salt thereof, is formulated in liquid form for delivery via continuous intravenous infusion, in situ infusion, intracoronary infusion, drip infusion, intracoronary bolus injection, a guiding catheter, or an IC micro-catheter. In other preferred embodiments, UTP, a derivative thereof, or a salt thereof, is formulated in liquid form for administration intravenously in legs for the determination of blood flow in the legs. UTP, a derivative thereof, or a salt thereof, can also be formulated in liquid form for delivery to the kidneys or via intracoronary infusion to the heart for the determination of blood flow.

Other suitable embodiments relate to a diagnostic composition comprising UTP, a derivative thereof, or a salt thereof, in a pharmaceutically acceptable aqueous carrier suitable for administration into a human patient, said composition containing said compound in the range of 10 to 1000 μmol/ml, preferably in the range of 50 to 400 μmol/ml, more preferably in the range of 100 to 360 μmol/ml. Examples of such compositions include:

Composition I: The concentration of UTP, a derivative thereof, or a salt thereof in the injectable composition can be between 10-2000 μg/ml, with a preferred diagnostic concentration between 20-500 μg/ml for IC use and 50-2000 μg/ml for iv use.

Composition II: The concentration of UTP, a derivative thereof, or a salt thereof can be controlled by adding sterile aqueous solution to dry powder UTPtrissalt or UTPNa$_3$ by techniques know to those skilled in the art to bring the concentration to about 100 μg/ml for IC and 300 μg/ml for iv use, the limit of its solubility under ambient conditions.

Composition 3: The concentration of UTP, a derivative thereof, or a salt thereof can be, in a clinical dose range, 10-1000 μg/ml, with preferred ranges of 25-500 μg/ml, 20-100 μg/ml, 40-150 μg/ml, 60-160 μg/ml, 80-360 μg/ml, 100-240 μg/ml, 120-480 μg/ml, and 150-600 μg/ml.

A related embodiment relates to a diagnostic composition wherein UTP, a derivative thereof, or a salt thereof, is in isotonic saline.

The rate of intravascular infusion of UTP, a derivative thereof, or a salt thereof, in increasing order of preference, is about 20 μg to about 2000 μg per minute, about 50 μg to about 600 μg, about 80 μg to about 360 μg, about 100 μg to about 500 μg, about 150 μg to about 400 μg, about 180 μg to about 360 μg, about 240 μg to about 360 μg, and about 180 μg to about 240 μg per minute.

UTP can be delivered by intracoronary infusion continually or by bolus via a guiding, FFR/thermodilution catheter or microinfusion catheter by stepwise dose escalation starting at 20 μg/min to induce maximal coronary blood flow, which corresponds to minimal distal coronary pressure. When steady-state hyperemia is achieved, preferably with continuous infusion (i.e., no further decrease in $P_d$ is occurring), FFR can be calculated as the ratio of the mean distal intracoronary pressure measured by the pressure wire to the mean arterial pressure measured by the coronary catheter. As such, a stepwise dose escalation from 20 μg/min to about 400 μg/min during continuous UTP infusion in any given assessed coronary artery should render the lowest possible $P_d$ and therefore the most accurate FFR value. Thus, hyperemic stimuli can be given as follows: an IC continuous infusion of UTP, a derivative thereof, or a salt thereof in incremental doses of 10, 20, 40, 80, 160, 240, 360 and 400 μg/min, in both the left and right coronary artery depending on lesion anatomy.

When UTP, a derivative thereof, or a salt thereof is administered via continuous intracoronary infusion, the rate of infusion maybe about 5 μg to about 600 μg/min, about 10 μg to about 550 μg/min, about 20 μg to about 500 μg/min, about 30 μg to about 450 μg/min, about 50 μg to about 400 μg/min, about 60 μg to about 360 μg/min, about 80 μg to about 360 μg/min, and about 180 μg to about 360 μg/min.

In terms of the solution to be infused, the UTP concentration can vary. Typically, the concentration will be from about 50 to about 100 μg/ml to be administered at a rate of 1-5 ml/min for about 3 to 5 minutes. Thus, a vial of pre-made solution of UTP should conveniently contain at least 10 ml of solution and could contain up to 25 ml. Larger amounts are possible but unnecessary for individual use.

If UTP is provided in solid form (e.g., lyophilized) in a vial it can be provided in individual use amounts according to the foregoing guidelines or in bulk and then dissolved prior to use in an appropriate amount of aqueous solvent.

The amounts given herein apply, on a UTP basis, to UTP salts and derivatives, but may need to be adjusted to account for differences in potency.

A typical practice is as follows: UTP solutions are freshly prepared from sterile lyophilized powder (2-mL ampoules containing 20 mg UTP as tris salt or trisodium salt) and then diluted appropriately in aqueous NaCl 0.9%. The solution can then be passed through a 0.2-microm Millipore filter is in a concentration of 50 microgram/ml which can then be pushed by an infusion rate of 1-5 ml/min in order to give a concentration of 50 to 250 microgram/min. If higher concentrations are needed to produce an even lower FFR the infusion rate can be increased even further, if for instance the patient has some of the known P2Y2 receptor polymorphisms (see, e.g., Janssens, R. et al, "Human P2Y2 receptor polymorphism: identification and pharmacological characterization of two allelic variants" Br J. Pharmacol. 1999 June; 127(3):709-16; and Buescher, R. et al, "P2Y2 receptor polymorphisms and haplotypes in cystic fibrosis and their impact on Ca2+ influx"*Pharmacogenet Genomics.* 2006 March; 16(3):199-205).

The drug may be administered at any time when the patient is in need of a hyperemic assessment such as FFR or other related diagnostic procedures, such as another form of nuclear imaging (including MPI), Ultrasound and echo cardiography, Fractional flow reserve, MRI/MRA, CT scan, PET scan, and ankle brachial index using mean arterial pressure.

Methods for Assessing Compromised Blood Flow

Methods of assessing compromised blood flow include nuclear imaging such as MPI, ultrasound and echo cardiography, fractional flow reserve, MRI/MRA, CT scan, PET scan, and ankle brachial index using mean arterial pressure. Compromised blood flow means any alteration in blood flow compared to normal blood flow, for example, an alteration caused by a stenosis or blood clot. Conversely, normal blood flow means blood flow that is uncompromised by, for example, a stenosis or a blood clot. A reference for normal blood flow may, for example, be developed by measuring the blood flow in at least 20 individuals with no suspected illnesses and determining the average. Conversely, some measurements are specific to the individual, e.g., FFR measurements. That is, the FFR value is solely dependent on the individual's ability to increase blood flow compared to when at rest.

In other contexts, a "reference value" may represent the value of blood flow associated with an abnormal condition. For example, when FFR is used to assess blood flow, the measured value is pressure differential between the distal end of a stenotic blood vessel segment under conditions of maximal hyperemia and the reference value is the corresponding pressure differential under similarly hyperemic conditions in the same vessel without stenosis. The connotation of "reference value" as used in a specific context will be apparent to one of ordinary skill in the art.

To determine whether a blood vessel has compromised blood flow, the blood flow can be assessed quantitatively by obtaining a value that correlates to blood flow in the vessel. This obtained value can then be compared to a reference value, which can be obtained, for example, from a similar blood vessel in the individual. It can then be determined whether the individual has a compromised blood flow based on the results of the comparison. This comparison allows for the determination of compromised blood flow in a blood vessel and may thereby assist in determining the presence of a stenosis and/or in diagnosing a disease or disorder, for example, Peripheral Artery Disease (PAD), coronary atherosclerosis, renal artery disease, atherosclerosis and/or ischemic heart disease.

The similar blood vessel may be any vessel with the same cross section area +/−20%. The similar vessel may thus, for example, be a similar blood vessel in the same individual, such as a vessel in same individual with the same cross section area +/−20%, and which has the same distance to the heart +/−20%. For example, if the blood vessel with suspected compromised blood flow is on the left side of the body, the similar vessel may be the corresponding vessel on the right side of the body. The similar vessel can, however, also be the same vessel in another healthy individual.

When blood flow is measured in the legs, the similar blood vessel with normal blood flow may be the vessel in one leg of an individual, wherein the vessel with a suspected compromised blood flow is in the other leg. When blood is measured in the heart, the similar blood vessel with normal blood flow may be one coronary artery in an individual, wherein the blood vessel with a suspected compromised blood flow is in another coronary artery.

Blood flow in the present invention can be assessed by any appropriate method known in the art. For example, blood flow can be assessed by fractional flow reserve (FFR) measurement, coronary flow reserve (CFR) measurement, mean arterial pressure (MAP) measurement, and arterial peak velocity (APV) measurement.

FFR was originally used in coronary catheterization to measure pressure differences across a coronary artery stenosis to determine the likelihood that the stenosis impedes oxygen delivery to the heart muscle, and is defined as the pressure behind (distal to) a putative stenosis relative to the pressure before the putative stenosis. The result is an absolute number; an FFR of 0.50 means that a given stenosis causes a 50% drop in blood pressure across the stenotic area. That is, FFR expresses the maximal flow down a vessel in the presence of a stenosis compared to the maximal flow in the hypothetical absence of the stenosis. During coronary catheterization, a catheter is inserted into the femoral (groin) or radial arteries (wrist) using a sheath and guidewire. FFR uses a small sensor on the tip of the wire (commonly a transducer) to measure pressure, temperature and flow to determine the exact severity of the lesion. This is done during maximal blood flow (hyperemia). A pullback of the pressure wire is performed, and pressures are recorded across the vessel.

FFR measurements can be carried out in any blood vessel in the body, for example, those in the legs, kidney, or heart. Any variation to the FFR method is contemplated to be within the scope of the present invention. In specific embodiments, the FFR method uses a guidewire or the tip of an IC microcatheter (Progreat Microcatheter System, Terumo, Japan).

Other catheters suitable for use in conjunction with the invention are disclosed in U.S. Provisional application Ser. No. 61/357,857, which is hereby incorporated by reference.

Advantages of using UTP over adenosine compounds in FFR include: the instantaneous achievement of steady state by UTP, making it feasible to perform accurate measurements and the pullback maneuver and bringing FFR procedure time down; the more accurate estimation of coronary blood flow, resulting in a more precise FFR because UTP produces close to maximum perfusion; UTP is not associated with side effects; UTP allows for a clear dose response curve, and UTP is short-acting, with no long-term effects. There is also emphasis on procedure-related complications and this new method therefore allows for repeated and easy measurement of FFR and can be performed via the radial artery on an outpatient basis, whereas intravenous adenosine will always require central venous access.

MAP is the perfusion pressure seen by organs in the body. Compromised blood flow may, in the order of preference, be reflected in a MAP of less than 60 mmHg, less than 50 mmHg, less than 40 mmHg, less than 30 mmHg, or less than 20 mmHg.

Average peak velocity (APV) may also be used in the present invention to determine the suspected compromised blood flow. APV in the range of 5 to 30 msec$^{-1}$ is indicative of compromised blood flow. Thus, in order of preference, APV of less than 30 msec$^{-1}$, preferably less than 20 msec$^{1}$, and more preferably less than 10 msec$^{-1}$ are considered indicative of compromised blood flow.

Other methods include stress tests, such as exercise, stress echocardiogram (e.g., dobutamine stress echocardiogram), myocardial scintigraphy/myocardial perfusion imaging (MPI), and the like [28-31].

Contraindications to dobutamine include: chest pain, high blood pressure, dizziness, nausea and extreme fatigue, ingestion of caffeine and treatment with beta blockers. Given that current risks of the stress echocardiogram procedure with dobutamine are not seen with UTP, dobutamine can be substituted with UTP, a derivative thereof, or a salt thereof in stress echocardiograms to assess blood flow in an blood vessel, to assess the heart's function and structures such as valve stenosis, to determine limits for safe exercise in patients who are entering a cardiac rehabilitation program and/or those who are recovering from a cardiac event, such as a heart attack (myocardial infarction, or MI) or heart surgery, to evaluate blood pressure during stress testing, to assess stress or exercise tolerance in patients with known or suspected coronary artery disease or to evaluate the cardiac status of a patient about to undergo surgery with for instance aortic stenosis.

MPI is the most widely used non-invasive method used for the detection of coronary artery disease, risk assessment, detection of viable myocardium, and evaluation of the effects of various therapeutic interventions. Adenosine and dipyridamole have been the mainstays of vasodilator stress testing. Dobutamine stress MPI is reserved for patients with contraindications for vasodilator testing with adenosine. However, all adenosine receptor agonists, including regadenoson, have been associated with bronchoconstriction, angina, severe hypotension and sinoatrial and atrioventricular nodal block because adenosine receptor agonists can depress the SA and AV nodes and may thus cause first-, second- or third-degree AV block, or sinus bradycardia; thus the drugs should not be given to patients with 2nd or 3rd degree AV block, or sinus node dysfunction. Importantly, UTP has none of these disadvantages, being more receptor selective and closer to maximal coronary blood flow and as there are no "adenine" effects of the current compound as it acts through a completely different purinergic receptor system (P2Y2). It is therefore much safer to use systemically because of limitation to systolic and diastolic blood pressure drops +no effect on the AV node. As such, UTP, a derivative thereof, or a salt thereof can be used in place of adenosine receptor agonists in MPI.

Methods for Detecting Blood Flow

Compromised blood flow may be determined with any device in the art useful for this purpose, such as a sphygmomanometer, blood pressure meter, and the like. Compromised blood flow may also be determined using techniques in the art useful for this purpose, such as the Color Doppler technique, Pulsed Doppler, Power Doppler, Doppler ultrasound, thermodilution, echo cardiography, plethysmography, and the like. Other methods suitable for use in the present invention include cardiac magnetic resonance imaging (MRI), computed tomography (CT) scan, cardiac catheterization, chest CT, myocardial perfusion scan, radionucleotide angiography, ultrafast CT scan, and the like.

Blood flow can also be monitored from an external position on the vessel by using, for example, a flow probe.

Methods for detecting blood flow can be combined with methods for assessing blood flow presented above.

Kit-of-Parts

All the materials and reagents required to determine the blood flow in an artery or vein of an individual with suspected compromised blood flow according to the present invention can be assembled together in a kit, such kit includes at least UTP, a derivative thereof, or a salt thereof as an active diagnostic ingredient, and instructions for the use thereof in an individual with suspected compromised blood flow according to any of the methods described herein.

In the above test kit, the reagents may be supplied from storage bottles or one or more of the test tubes may be pre-filled with the reagents or controls.

The components of the kit, particularly UTP, a derivative thereof, or a salt thereof, may be provided in dried or lyophilized forms. When reagents or components are provided as a dried form, reconstitution generally is by the addition of a suitable solvent. It is envisioned that the solvent also may be provided in another container means. Alternatively, UTP, a derivative thereof, or a salt thereof can be provided in ready-to-use (pre-sterilized) form after reconstitution at the use point. The UTP, a derivative thereof, or a salt thereof can also be provided in suspended form, i.e., already suspended in the suitable solvent.

The kits of the present invention also will typically include a means for containing the reagents such as vials or tubes in close confinement for commercial sale such as, e.g., injection or blow-molded plastic containers into which the desired vials are retained.

The kits will also comprise a set of instructions on how to determine suspected compromised blood flow according the methods of the invention.

Different kits are provided with components, reagents and instructions suitable for the preferred modes of delivery described herein above, including delivery via continuous intravenous infusion, in situ infusion, intracoronary infusion, drip infusion, intracoronary bolus injection, a guiding catheter, or an IC micro catheter. Guiding catheter(s) and/or microcatheter(s) may also be provided with the kits.

Examples of suitable commercially available catheters for use with the kits are: ComboWire® and FloWire® Doppler Guide Wire (Volcano Corporation); PressureWire™ Certus and PressureWire™ Aeris Wireless (St. Jude Medical, Inc.).

EXAMPLES

Example 1

Systemic Infusion of UTP for Myocardial Perfusion Imaging (Prophetic)

MPI is a form of functional cardiac imaging that may be used for the diagnosis of ischemic heart disease. The underlying principle is that under conditions of stress, diseased myocardium receives less blood flow than normal myocardium. MPI is one of several types of cardiac stress tests.

A cardiac specific radiopharmaceutical, such as $^{99m}$Tc-tetrofosmin (Myoview, GE healthcare) or $^{99m}$Tc-sestamibi (Cardiolite, Bristol-Myers Squibb) is administered. Following this, the heart rate and coronary blood flow is raised to induce myocardial stress by systemic infusion of UTP, a derivative thereof, or a salt thereof.

SPECT imaging performed after stress reveals the distribution of the radiopharmaceutical, and therefore the relative blood flow to the different regions of the myocardium. Diagnosis is made by comparing stress images to a further set of images obtained at rest (the reference value). As the radionuclide redistributes slowly, it is not usually possible to perform both sets of images on the same day, hence a second attendance is required 1-7 days later. However, if stress imaging is normal, it is unnecessary to perform rest imaging, as it too will be normal—thus stress imaging only is normally performed.

MPI has been demonstrated to have an overall accuracy of about 83% (sensitivity: 85%; specificity: 72%) and is comparable with (or better than) other non-invasive tests for ischemic heart disease.

Example 2

Local Infusion of UTP Via Guiding Catheter in the Coronary Arteries in Humans with Coronary Artery Disease The study was performed in 23 patients undergoing elective coronary arteriography (CAG) due to repetitive episodes of typical ischemic chest pain or in patients with recent Non-ST Elevated Myocardial Infarction (>2 days from entry into study). In eligible patients with uni- or multivessel coronary artery disease, lesions with stenosis of at least 50% of their diameter and that were thought to require PCI on the basis of angiographic appearance and clinical data were identified.

Dose/Response Protocol

In the first part of the experiment, FFR and Coronary Flow (velocity, CFR) were measured after the induction of coronary hyperemia by a continuous intracoronary infusion of UTP (Jena Bioscience GmbH, Germany) and adenosine in random order in a guide catheter (5F catheter, Cordis Corp.). Two UTP doses of 240 and 360 µg/min were tested. UTP was prepared by dissolving 100 mg of UTP trisalt (Sigma Aldrich) in 50 ml isotonic NaCl. Of this 50 ml solution, 40 ml was filter sterilized and added to sterile NaCl solution to a final volume of 500 ml, providing a 0.16 mg/ml concentration. 8-10 50 ml syringes of this solution can be prepared (2 syringes per FFR study). 3 ml/min=480 µg/min=0.9 µmol/min. Subjects thus received either 1.5 ml/min of UTP infusion or 2.25 mL/min of UTP infusion for a total of 3 minutes each. Patients also received adenosine (Sigma Aldrich) in the same eqipotent concentration.

All measurements were performed on at least 2 separate occasions to achieve a reproducible result with a mean value calculated. After each measurement, care was taken that APV returned to baseline before the administration of the next dose. For all measurements using both drugs and both routes of administration, changes in heart rate, blood pressure, and ECG were recorded.

In the second part of the experiment, a full dose response curve was generated for a gradual incremental increase in continuous UTP infusion while both CFR and FFR were measured simultaneously prior to percutaneous coronary intervention (PCI). Hyperemia was induced at 80 µg/min of continuous intracoronary UTP and adenosine, and the flow reserve values were compared (Table 1).

In the third part of the experiment, both CFR and FFR were measured simultaneously after percutaneous coronary intervention (PCI). Hyperemia was induced by either 240 or 360 µg/min of continuous intracoronary UTP and equipotent adenosine, and the flow reserve values were in some patients compared with the hyperemic response of a complete, proximal coronary occlusion for 30 s.

Calculations of Fractional and Coronary Flow Reserve

FFR is defined as the ratio of hyperemic flow in a stenotic artery to the hyperemic flow in the same artery if there was no stenosis present. FFR therefore expresses maximum hyperemic blood flow in a stenotic vessel as a fraction of its normal value. FFR can be calculated from intracoronary pressure measurements obtained during maximal hyperemia by the following equation: $FFR = P_d - P_v / P_a - P_v \rightarrow P_d / P_a$, where $P_a$ is the mean proximal coronary pressure (mean aortic pressure), $P_d$ is the mean distal coronary pressure, and $P_v$ is the mean central venous pressure. The coronary flow (velocity) reserve is the ratio of maximum to baseline hyperemic coronary flow velocity and is used as a surrogate for CFR. Using the Volcano Combomap®, APV throughout the cardiac phase was measured and CFR calculated from $APV_{(hyperemia)}/APV_{(basal)}$.

Results

The results of this experiment are shown in FIGS. 1-4 and 8.

Comparison of IC adenosine and IC UTP continuous adenosine infusion in a dose response curve of six patients:

TABLE 1

| | FFR | | | | | |
|---|---|---|---|---|---|---|
| Patient | BL ado | ADO 80 | ADO 160 | ADO 240 | ADO 320 | ADO 400 |
| 1.00 | 0.98 | | | 0.87 | 1.02 | 1.01 |
| 2.00 | 0.91 | | 0.96 | 0.91 | 0.89 | 0.89 |
| 3.00 | 0.88 | 0.88 | 0.75 | 0.71 | 0.70 | |
| 4.00 | 0.87 | 0.83 | 0.80 | 0.81 | 0.79 | |
| 5.00 | 0.97 | 0.95 | 0.95 | 0.94 | 0.96 | |
| 6.00 | 0.79 | 0.76 | 0.60 | 0.60 | 0.54 | 0.56 |
| Mean | 0.90 | 0.86 | 0.81 | 0.81 | 0.82 | 0.82 |
| 2SEM | 0.06 | 0.08 | 0.13 | 0.11 | 0.14 | 0.27 |

| Patient | BL UTP | UTP 80 | UTP 160 | UTP 240 | UTP 320 | UTP 400 |
|---|---|---|---|---|---|---|
| 1.00 | 1.01 | | | 0.89 | 0.90 | 0.90 |
| 2.00 | 0.92 | | 0.90 | 0.89 | 0.89 | 0.92 |

TABLE 1-continued

| | FFR | | | | | |
|---|---|---|---|---|---|---|
| 3.00 | 0.88 | 0.73 | 0.73 | 0.73 | 0.72 | |
| 4.00 | 0.85 | 0.79 | 0.79 | 0.79 | 0.77 | |
| 5.00 | 1.01 | 0.88 | 0.86 | 0.87 | 0.86 | |
| 6.00 | 0.78 | 0.56 | 0.56 | 0.55 | 0.56 | 0.56 |
| Mean | 0.91 | 0.74 | 0.77 | 0.79 | 0.78 | 0.79 |
| 2SEM | 0.07 | 0.13 | 0.12 | 0.11 | 0.11 | 0.23 |

It is clear that at any given level of continuous UTP infusion, the FFR value is lower in comparison to the same equipotent level of adenosine. The lowest FFR level using adenosine is 0.81±0.11, however the lowest level for UTP is 0.74±0.13; (P<0.05). As stated, the doses of adenosine and UTP are different numerically because the preparations have been made to be equipotent.

The times to induction of maximal hyperemia in all IC continuous UTP infusion rates were shorter than that of IC continuous adenosine infusion. As shown in all 23 patients, FFR was significantly decreased with IC 240 µg/min infusion of UTP in comparison to adenosine infusion (p=0.003) (FIG. 1). Consistent with this, $P_d$, or mean distal coronary pressure, was also significantly decreased with UTP infusion compared to adenosine infusion.

It has previously been shown that IC continuous adenosine infusion is more effective in inducing maximal coronary hyperemia than IV continuous adenosine infusion [8]. Particularly early induction of optimal coronary hyperemia has a great advantage in repetitive measurement of FFR. However, in comparison to UTP, adenosine is not as vasodilatatorily potent presumably due to differences in activated receptor types, affinity for the respective receptors, and amounts infused. Thus, although the IC adenosine continuous infusion method for FFR measurement is an accepted standard method for inducing maximal and steady-state coronary hyperemia, it does not induce maximal hyperemia when compared with UTP administration.

None of the UTP-treated patients in the current trial had chest pain, dyspnea, second or 3 degree A-V block or changes in systemic blood pressure and heart rate during IC continuous UTP infusion, whereas most patients felt uncomfortable chest pain and 2 patients had 3 degree A-V block during adenosine infusion. Our IC UTP infusion method is thus safe for inducing coronary hyperemia without any systemic complications compared to the IC and IV adenosine infusion method.

The optimal dose of UTP for achieving maximal coronary hyperemia by our guide catheter method was UTP in concentrations of 80-400 µg/min. Intracoronary UTP infusion at these doses can induce more rapid and more potent coronary hyperemia than previous methods compared with equipotent IC adenosine doses which are more potent than the standard IV adenosine concentration of 140 µg/min. No further decrease in FFR was observed after IC UTP infusion at >360 µg/min.

We conducted this study in most patients where FFRs were present in the gray zone between 0.76 and 0.80 assessed by IC bolus adenosine injection, but where IC infusion of UTP lowered the FFR even further due to bigger post stenotic vasodilatation. The preferred infusion rate for inducing maximal hyperemia by the IC continuous UTP infusion method is thus ~80 to 400 µg/min.

The results collectively demonstrate that IC continuous infusion of UTP is safe and useful for inducing optimal coronary hyperemia without any additional procedure; IC UTP infusion is a more potent vasodilatator than IC adenosine infusion in equipotent concentrations; while previous studies have shown that IC Ado=IC ATP infusion>IV adenosine infusion, the findings of the present study suggest that UTP>adenosine=ATP; and IC UTP infusion is not associated with adverse effects in contrast to IC or IV adenosine or ATP infusion.

Example 3

Local Infusion of UTP Via a Microcatheter in the Coronary Arteries in Humans with Coronary Artery Disease As described previously, inducing stable maximal coronary hyperemia is essential for measurement of fractional flow reserve (FFR). This second experiment in a similar patient group evaluated the differential efficacy of intracoronary (IC) continuous adenosine infusion vs. IC continuous uridine triphosphate (UTP) infusion via a microcatheter for inducing steady state maximal coronary hyperemia. The present study was designed to evaluate the safety and effectiveness of the equimolar concentrations of UTP vs. adenosine infusion for use in the FFR method. Time to achievement of steady-state, impact of maximal hyperemia (lowest FFR) for the different compounds and side effects were recorded in 10 patients with intermediate coronary lesions. FFR was measured consecutively by IC continuous adenosine or UTP infusion using a microcatheter to bypass the proximal pressure transducer. The IC microcatheter (Progreat Microcatheter System, Terumo, Japan) used was positioned at the coronary ostium, and FFR was then measured by increasing IC continuous adenosine or UTP infusion rates in equimolar concentrations from 10 to 400 μg/min via the microcatheter.

After femoral catheterization, coronary angiography was performed with the standard femoral approach. Heparin was administered according to standard procedures.

Intracoronary nitroglycerin (0.2-0.3 mg) was administered before the control angiograms were made in the microcatheter study. Heart rate and arterial pressure were continuously monitored throughout the procedure. After a guiding catheter (5F catheter, Cordis Corp.) without side holes was positioned at the coronary ostium, coronary angiograms were obtained from multiple projections. Quantitative coronary analysis was performed by using an independent analyzer blinded to the results of FFR using a computer-assisted, automated computerized edge-detection algorithm (Siemens Medical System). The external diameter of the contrast-filled catheter was used as a calibration standard. Minimal luminal diameter, vessel diameter of the reference segment, and the percent diameter stenosis at end diastole were measured from the worst-view trace. After coronary angiography, a 0.014-in. pressure wire (Combowire, Volcano Corporation, US) was advanced distally to the stenosis through a 6F guiding catheter. In the microcatheter study, an IC bolus injection of nitroglycerin (0.2-0.3 mg) was given before advancing the pressure wire through the stenosis in order to avoid any mechanically-induced coronary vasoconstriction. The pressure wire was externally calibrated and then advanced to the distal tip of the catheter. It was verified whether equal pressure was recorded at both the catheter and the pressure wire. The pressure wire was advanced through the coronary catheter, introduced into the coronary artery, and positioned distal to the stenosis.

Distal coronary pressure ($P_d$) and proximal coronary pressure ($P_a$) were measured at baseline and at maximal hyperemia (adenosine vs. UTP) simultaneously. Fractional flow reserve was calculated by dividing mean $P_d$ by mean $P_a$ during maximal hyperemia. The time to optimal vasodilatation (time needed to reach >90% of the minimal value of $P_d/P_a$ after administration of the adenosine or UTP) was computed in order to assess whether procedure time was prolonged. The hyperemic stimuli were given as follows: an IC continuous infusion of adenosine or UTP in incremental doses of 10, 20, 40, 80, 160, 240, 360 and 400 μg/min, in both the left and right coronary artery depending upon lesion anatomy. The dosages were increased stepwise by IC continuous infusion with the microcatheter where the stepwise dose increase was recorded continuously without breaks. After each stepwise increase, FFR and CFR were recorded automatically. The next hyperemic stimulus UTP vs adenosine was given when $P_a$, $P_d$, and heart rate returned to their baseline values.

As described above, the results showed that the fractional flow reserve measured by the IC continuous UTP infusion method was significantly lower than that of the IC continuous adenosine infusion method. Also, induction time to optimal coronary hyperemia by our method was also shorter than that by the IC continuous adenosine infusion method. As stated above, the induction of optimal coronary hyperemia has a great advantage in repetitive measurement of FFR and our method makes it possible to measure FFR repetitively and easily within a short period of time when compared with previous methods. None of the patients had chest pain in the UTP group but nearly all felt angina in the adenosine group due to P1 pain receptor stimulation. Also, some patients had a transient second degree A-V block during IC adenosine infusion. There was no difference in systemic blood pressure and heart rate during IC continuous UTP or adenosine infusion. The IC UTP infusion method is thus safe for inducing coronary hyperemia without any systemic complications compared to the IC adenosine infusion method.

Figure 5:
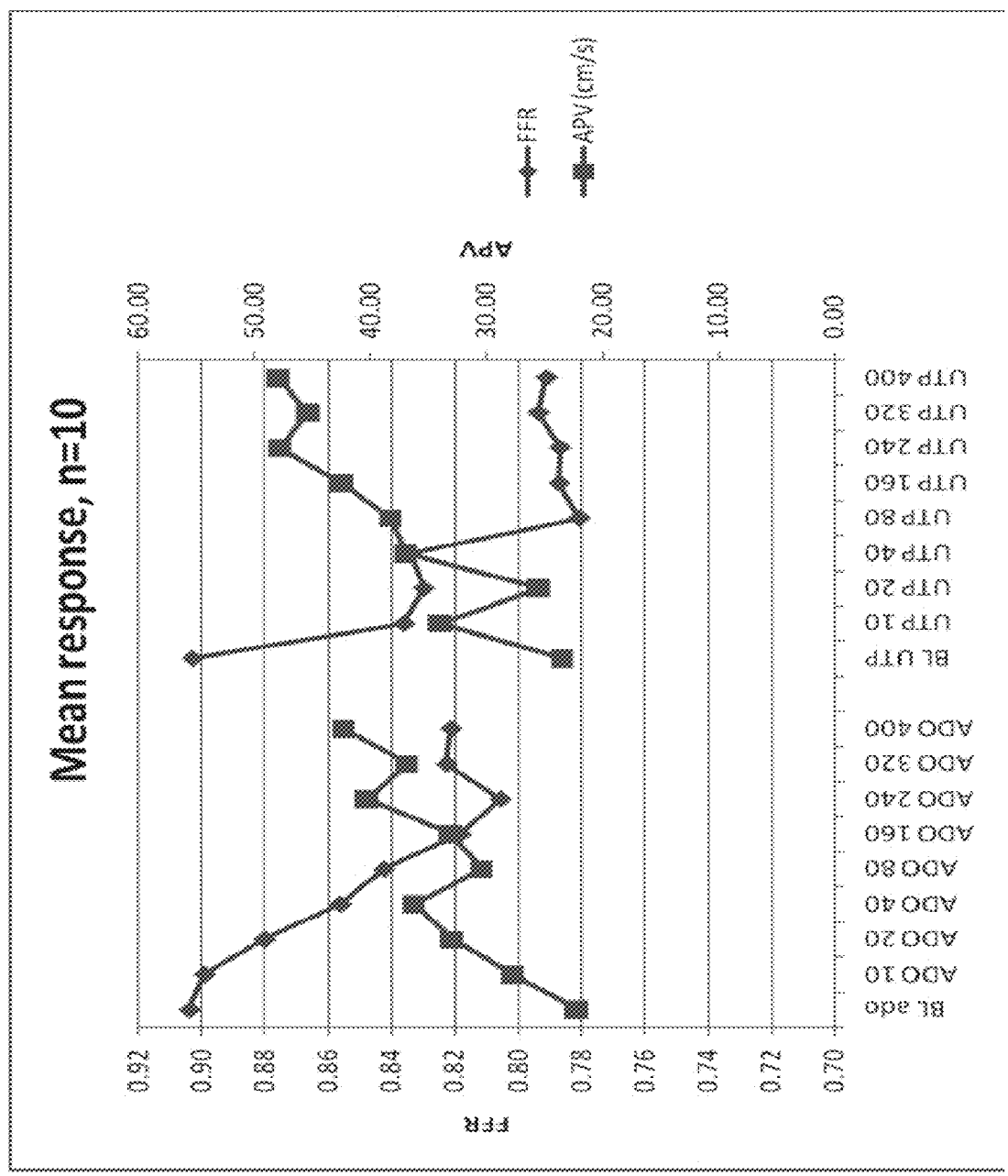
FIG. 5 is a graph showing mean FFR and average peak velocity (flow) response during micro-catheter infusion of adenosine and UTP. The graph clearly demonstrates that at any given equipotent infusion, UTP>adenosine and adenosine never reaches as low an FFR as UTP.

The optimal dose of UTP for achieving maximal coronary hyperemia and thereby the lowest FFR by the UTP method was approximately 80 μg/min for UTP and 240 μg/min for adenosine (FIG. 5). However, no intracoronary adenosine infusion produced as low FFR levels at any given concentration as that achieved during UTP infusion, meaning that adenosine, even at its highest concentration, rendered a higher FFR than UTP. UTP above 80 μg/min did not further lower FFR, and must thus be assumed to be the correct amount to be infused. However, given that some patients may be more or less responsive to this dose depending upon their number of effective receptors and distribution, it is recommended that the starting dose should be around 50 μg/min and then increased incrementally until the lowest level of FFR is achieved. In this manner, the dose range can be individualized according to any given patient's need for an optimal diagnosis.

All patients tolerated UTP without side effects, but nearly all patients experienced side effects during the adenosine procedures. FFRs measured by UTP infusion were significantly lower than those by IC adenosine infusion (P<0.05). Intracoronary UTP infusion was also able to shorten the time to induction of optimal and steady-stable hyperemia which also lasted slightly longer (~20 seconds) with UTP compared to adenosine infusion.

Table 2

TABLE 2

| | FFR | | | | | | | | |
|---|---|---|---|---|---|---|---|---|---|
| Patient | BL ado | ADO 10 | ADO 20 | ADO 40 | ADO 80 | ADO 160 | ADO 240 | ADO 320 | ADO 400 |
| 1.00 | 0.98 | | | | | | 0.87 | 1.02 | 1.01 |
| 2.00 | 0.91 | | | | | 0.96 | 0.91 | 0.89 | 0.89 |
| 3.00 | 0.88 | | | | 0.88 | 0.75 | 0.71 | 0.70 | |
| 4.00 | 0.87 | | | | 0.83 | 0.80 | 0.81 | 0.79 | |
| 5.00 | 0.97 | | | | 0.95 | 0.95 | 0.94 | 0.96 | |

TABLE 2-continued

FFR

| Patient | BL UTP | UTP 10 | UTP 20 | UTP 40 | UTP 80 | UTP 160 | UTP 240 | UTP 320 | UTP 400 |
|---|---|---|---|---|---|---|---|---|---|
| 6.00 | 0.79 | | | | 0.76 | 0.60 | 0.60 | 0.54 | 0.56 |
| 7.00 | 0.89 | 0.81 | 0.75 | 0.73 | 0.71 | 0.68 | | 0.70 | |
| 8.00 | 0.90 | 0.94 | 0.94 | 0.94 | 0.94 | 0.95 | | 0.95 | |
| 9.00 | 0.86 | 0.86 | | 0.82 | 0.82 | 0.85 | | 0.86 | |
| 10.00 | 0.98 | 0.99 | 0.95 | 0.94 | | | | | |
| Mean | 0.90 | 0.90 | 0.88 | 0.86 | 0.84 | 0.82 | 0.81 | 0.82 | 0.82 |
| 2SEM | 0.04 | 0.08 | 0.13 | 0.11 | 0.07 | 0.10 | 0.11 | 0.10 | 0.27 |

| Patient | BL UTP | UTP 10 | UTP 20 | UTP 40 | UTP 80 | UTP 160 | UTP 240 | UTP 320 | UTP 400 |
|---|---|---|---|---|---|---|---|---|---|
| 1.00 | 1.01 | | | | | | 0.89 | 0.90 | 0.90 |
| 2.00 | 0.92 | | | | | 0.90 | 0.89 | 0.89 | 0.92 |
| 3.00 | 0.88 | | | | 0.73 | 0.73 | 0.73 | 0.72 | |
| 4.00 | 0.85 | | | | 0.79 | 0.79 | 0.79 | 0.77 | |
| 5.00 | 1.01 | | | | 0.88 | 0.86 | 0.87 | 0.86 | |
| 6.00 | 0.78 | | | | 0.56 | 0.56 | 0.55 | 0.56 | 0.56 |
| 7.00 | 0.84 | 0.72 | 0.71 | 0.72 | 0.71 | 0.71 | | 0.69 | |
| 8.00 | 0.94 | 0.95 | 0.95 | 0.95 | 0.97 | 0.92 | | 0.90 | |
| 9.00 | 0.89 | 0.84 | | 0.83 | 0.83 | 0.83 | | 0.84 | |
| 10.00 | | | | | | | | | |
| Mean | 0.90 | 0.84 | 0.83 | 0.83 | 0.78 | 0.79 | 0.79 | 0.79 | 0.79 |
| 2SEM | 0.05 | 0.14 | 0.24 | 0.13 | 0.10 | 0.08 | 0.11 | 0.08 | 0.23 |

Dose response curve of intracoronary adenosine vs. UTP

These results collectively suggest that IC continuous UTP infusion using an IC microcatheter may be safe and useful for inducing optimal coronary hyperemia for the individual patient without any additional procedure. There are no obvious contraindications or cautions to consider since UTP carries no side effects; UTP is more receptor selective and has a faster and slightly longer steady state; UTP produces maximal hyperemia, which is close to post occlusion hyperemia, thus allowing for a more accurately estimate of maximal coronary blood flow and rendering a more precise FFR calculation.

Not only can UTP be used in all patients following normal guidelines for FFR use, it can be further extended to include those patients who have contraindications to the use of adenosine and who for this reason would not normally be FFR tested.

Example 4

Systemic Infusion of UTP in Pigs for Using UTP as a Coronary, Renal or Peripheral Dilator in Diagnostic Hyperemic Methods In the present study, the hemodynamic response in the pulmonary and systemic circulation was tested, as well as the effect of central intravenous infusions of ATP, ADP, ADO, and UTP on the heart.

Infusion rates were aimed at exerting a pronounced systemic response in the lowering of arterial blood pressure, but avoiding a total circulatory collapse.

Methods: 10 healthy female pigs (Department of Experimental Medicine and Surgery, University of Copenhagen, Denmark) bred as a combination of the Danish Landrace (⅓) and Yorkshire (⅔), with a medium weight of 41±2 kg were investigated.

Mean arterial blood pressure (MAP) was obtained from the catheter in arcus aorta with the transducer (Pressure Monitoring Kit, Baxter, Deerfield, Ill., USA) positioned at the level of the heart. The left femoral artery was subsequently exposed and an ultrasound doppler probe attached for peripheral femoral artery flow measurements (CM-4000, Cardiomed, Norway). MAP, HR and peripheral flow were monitored and data continuously collected using a PowerLab system (Adinstruments, Australia). Cardiac Output (CO) was determined in triplicates by thermodilution, following an injection of 10 ml of cooled saline solution. Blood samples were withdrawn from catheters in aorta and the right atrium at baseline and at steady state when MAP had decreased maximally or by ~50%. Calculated variables were: stroke volume of the heart (SV=CO/HR), pulmonary vascular resistance (PVR=(MPAP−PCWP)/CO), systemic vascular resistance (SVR=(MAP−MRAP)/CO), leg vascular conductance (LVC=LBF/(MAP−MRAP)), and arterial (aorta) and mixed venous (pulmonary artery) oxygen content (Hb*1.34*$O_2$ saturation). In the calculation of LVC, MRAP was used as an estimate of mean femoral venous pressure (MFVP), as MRAP was found in a series of measurements to equal MFVP, as estimated in 10 supine pigs. As a potential estimate for myocardial oxygen demand the rate pressure product (RPP=MAP*HR) was also calculated.

Drug infusions: Each animal was administered the nucleotides ATP, UTP, ADP (Sigma, St. Louis, Mo., USA) and ADO (Item Development AB, Stocksund, Sweden), through the internal jugular vein in the right atrium, in random order following blinded allocation. The nucleotides and ADO were prepared by dissolving in saline so as to achieve the target concentration of ATP (40±0.5 μmol/min), ADP (43±8 μmol/min), UTP (up to 1,600 μmol/min), and ADO (73±7 μmol/min). The nucleotides were infused in increasing dosages at 2 min intervals aiming at reducing MAP by maximally ~50%. Thereafter, that specific infusion rate was maintained for ~3-5 min. After each intervention the animal rested for ~30 min, allowing resting cardiovascular variables to be reestablished. Thereafter, a new cycle of nucleotide infusion was administered. In the present study we aimed to allow the drugs to reduce MAP by ~50%, but without inducing a hemodynamic and circulatory collapse, to simulate a pronounced state of systemic vasodilation, as may be observed for instance in a shock condition.

Results

Infusion Rates

Figure 6:
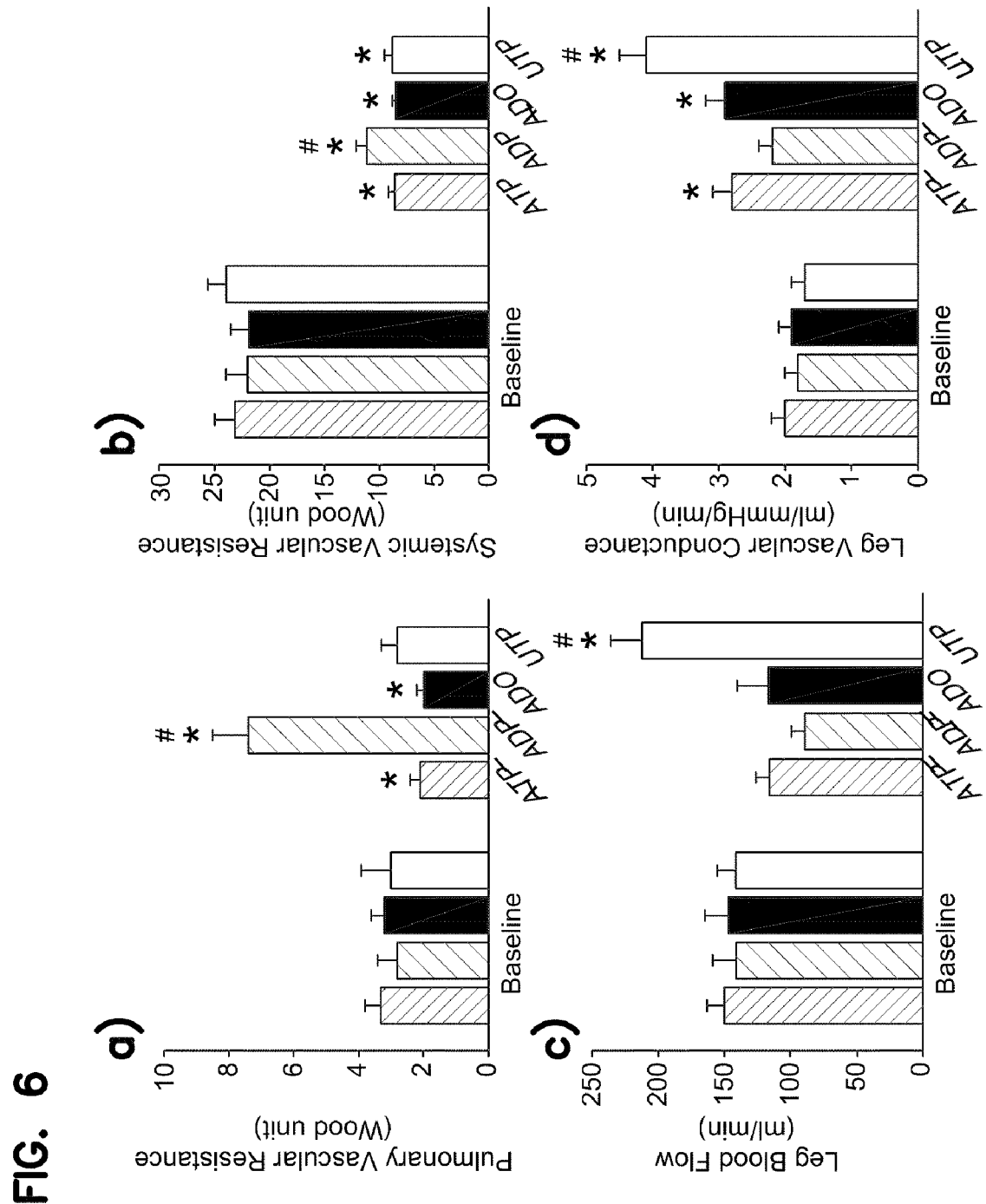
FIGS. 6A through 6D are graphs showing hemodynamic variables (pulmonary vascular resistance, systemic vascular resistance, leg blood flow and leg vascular conductance) during systemic UTP infusion in comparison to adenosine, ATP, and ADP. UTP increases blood flow and leg vascular conductance much more than the other compounds, making it suitable for assessment of peripheral artery disease because the blood flow increase may simulate exercise.
Figure 7:
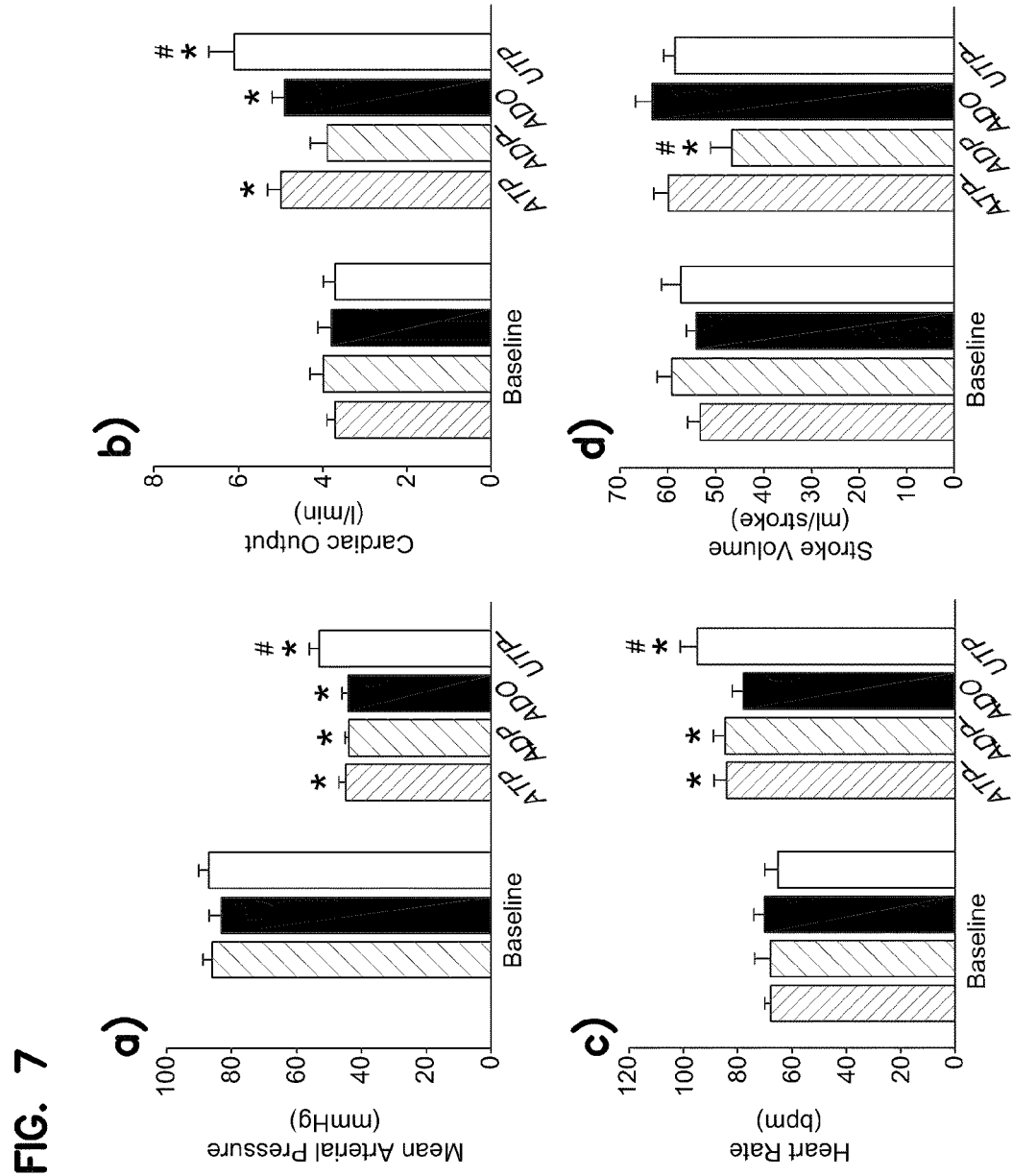
FIGS. 7A through 7D are graphs show hemodynamic variables (mean arterial pressure, cardiac output, heart rate and stroke volume) during systemic UTP infusion in comparison to adenosine, ATP and ADP. UTP does not lower blood pressure as much as the other compounds but increases cardiac output and HR, more resembling exercise, thus making it a suitable stress agent for studies involving myocardial perfusion imaging.
Figures 8, 9:
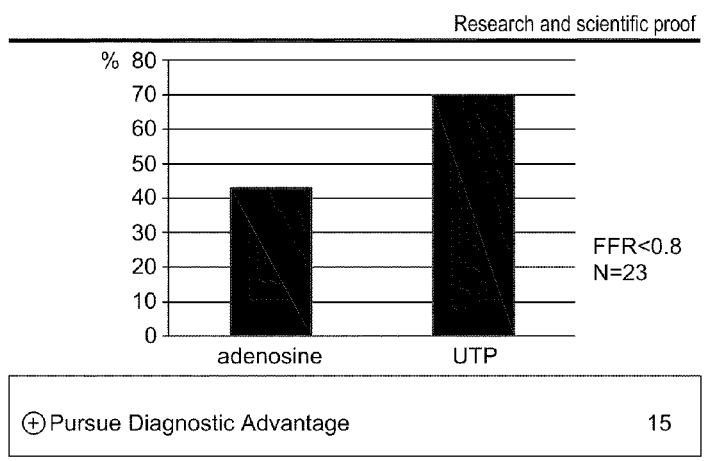
FIG. 8 is a graph showing that use of UTP alters clinical decision making more than adenosine because it determines the FFR more accurately. (n=23). This would lead to a diagnostic advantage.
FIG. 9 is a diagram of indications and methods contemplated to be within the scope of the present invention.

There were no significant differences in any of the baseline conditions before infusions of ATP, ADP, ADO or UTP (FIGS. 6 and 7). At target MAP, corresponding to a ~50% reduction in baseline MAP, ATP and ADP were infused at similar rates (40.2±0.5 and 43.2±7.7 μmol/min, p=ns), whereas ADO was infused at a higher rate (72.7±6.6 μmol/min, p<0.05). A further increase in ATP, ADP and ADO infusion rate, in contrary to UTP, could lower MAP below the target ~50% reduction in MAP, requiring careful monitoring during dosage titration. In an attempt for UTP to reach ~50% reduction in MAP, UTP infusion rate was increased as high as 1.600 μmol/min in two animals. However, UTP infusion did not decrease MAP more than ~35%. This reduction was also obtained at much lower UTP infusion rates (86.5±18.2 μmol/min). Since an increase in the dosage of UTP did not decrease MAP further in those animals, the UTP infusion rate was not increased beyond this dose in the remaining experiments, when this drop in MAP was reached (FIG. 7a).

Nucleotides and their Effects on Pressures, CO, HR and SV. (FIG. 7)

During infusion of ATP, ADP and ADO, MAP was lowered by 47.4±1.7, 48.4±1.2 and 47.2±1.5%, respectively, from stable baseline values (p<0.05) (FIG. 7a). However, during UTP infusion, MAP was only lowered by 35.0±3.2% (p<0.05) (FIG. 7a). Furthermore ATP, ADO and UTP increased CO by 35.1±6.9, 31.4±9.9 and 72.5±15.2%, respectively (p<0.05) (FIG. 7b). ADP infusion did, however, not alter CO (p=ns). The CO increase during UTP infusion was furthermore greater than the increase in CO during infusion of ATP and ADO (p<0.05). In addition, ATP, ADP and UTP increased HR with 23.0±5.7, 26.6±4.6 and 51.1±9.0%, respectively, from stable baseline values (p<0.05) (FIG. 7c). ADO however, did not increase (p=ns) HR. The increase in HR was also greater for UTP than for the other nucleotides (p<0.05). ATP, ADO and UTP infusion did not significantly change SV (p=ns) (FIG. 7d). However, ADP infusion decreased SV by 21.1±5.6% (p<0.05).

Nucleotides and their Effects on Vascular Resistance, Conductance and Blood Flow.

ATP and ADO infusion decreased PVR by 37.8±4.9 and 34.3±2.6%, respectively, from stable baseline values (p<0.05) (FIG. 7a). There was no significant difference (p=ns) in the PVR change between the ATP and ADO infusions. UTP did not significantly alter (p=ns) PVR. On the contrary, ADP markedly increased PVR by 156.7±38.3% (p<0.05). PVR furthermore rose early in the ADP titration procedure even during low infusion rates and continued to increase dose dependently to 7.3±1.2 Wood Unit (p<0.05).

ATP, ADP, ADO and UTP infusion all decreased SVR by 61.6±2.1, 49.5±2.0, 59.0±3.0 and 62.9±2.6%, respectively, from stable baseline values (p<0.05) (FIG. 3b). There was no significant difference (p=ns) in the SVR change between trials. ATP, ADP and ADO decreased LBF by 22.7±4.2, 34.9±10.2 and 19.4±10.7%, respectively, from stable baseline values (p<0.05) (FIG. 6b). UTP however increased LBF by 53.7±17.8% (p<0.05). There was no difference (p=ns) in the change in LBF between these trials (FIG. 6c). LVC showed a tendency to increase for all nucleotides, but this increase was only significant for ATP, ADO and UTP (p<0.05); with an increase by 44.7±8.7, 56.4±12.9 and 150.0±17.1%, respectively, from stable baseline values (p<0.05). UTP increased LVC more than the other nucleotides (p<0.05).

The Vasoactive Effect of ADP, ATP, UTP and Adenosine in the Leg (FIG. 6)

The vasodilator potency in the peripheral circulation revealed that ADP>ATP=ADO. Thus ATP, ADP and ADO decreased LBF with 22.7±4.2, 34.9±10.2 and 19.4±10.7%, respectively, from stable baseline values (p<0.05). UTP however increased LBF by 53.7±17.8% (p<0.05) (FIG. 6c), presumably because of a high increase in CO and a lesser degree of systemic pressure reduction. LVC showed a tendency to increase for all nucleotides, but this increase was only significant for ATP, ADO and UTP; with an increase by 44.7±8.7, 56.4±12.9 and 150.0±17.1%, respectively, from stable baseline values (p<0.05).

The study identified the unique differential properties of the nucleotides ATP, ADP, ADO and UTP in the pulmonary, peripheral and systemic circulation. This is the first study to simultaneous compare the vasodilatory potency of nucleotides when infused in the right atrium. Previous studies have shown that ATP, ADP, ADO and UTP all induce local vasodilation when infused in the femoral artery and intravenous infusions can mediate a decreases in MAP but none of these studies have compare the relative potency of all of these nucleotides. With regards to the dose of the nucleotides needed to reduce MAP by ~50%, no difference in potency was observed for ATP and ADP, despite different purinergic receptor affiliation; where ADP predominantly stimulates $P2Y_1$, $P2Y_{12}$ and $P2Y_{13}$ receptors; and ATP predominantly stimulates P2X, $P2Y_2$, $P2Y_4$ and $P2Y_{11}$ receptors. ADO, predominantly stimulating P1 receptors, was less potent than ADP and ATP, thus requiring a higher infusion rate to produce the same decrease in MAP. This makes it unlikely that the effect of ATP and ADP was due to the dephosphorylated metabolites of these substances. UTP, stimulating $P2Y_2$ and $P2Y_4$ receptors, was unable to produce the targeted ~50% drop in MAP, due to a marked dose dependent rise in HR and CO. These results differs from previous findings with intra-arterial nucleotide infusions, where ATP and UTP were found to be equipotent, and even more potent than ADO and ADP. This may be due to that the passage of the nucleotides through the pulmonary and coronary circulation affects the MAP response, differently from when infused intra-arterially.

The study also showed that UTP do not change PVR, despite an increase in MPAP, as it was counterbalanced by an increase in CO, at an unaltered PCWP. Previous studies have also suggested that ATP, but not UTP, mediate vasodilation in the pulmonary artery, in the presence of a functional endothelium. Although previous studies have shown that ATP and UTP increase myocardial contractility, probably through P2X, P2Y2, P2Y6 and P2Y11-like receptors the present study only detected CO increases during infusions of ATP, ADO and UTP; and to the greatest extent for UTP. ATP, ADP and UTP all increase HR, whereas ADO do not change HR significantly. UTP furthermore increases HR significantly more than ATP and ADP.

Relevance for diagnostic use: These results collectively suggest that when UTP is infused intravenously in the systemic circulation it: increases cardiac output (CO) by ~70% due to increases in HR, thus resembling an exercise condition; it has a tendency to decrease rate pressure product by ~10%, thereby being safe for patients with ischemia; and importantly does not produce arrhythmias (missed beats, VT, SVT or AV nodal block). Furthermore, UTP increases leg blood flow by ~50% presumably because of a higher increase in CO (such as during exercise) and has a lesser degree of systemic pressure reduction compared to other adenine compounds, making it suitable for use with indications such as aorta stenosis, peripheral arterial disease (PAD), or kidney stenosis with methods such as myocardial perfusion imaging, echo or MRI). Furthermore, because it increases leg vascular conductance by ~150% (only ~50% with adenosine), UTP is ideal for PAD diagnosis because it mimics exercise-induced vasodilatation.

Example 5

The following data demonstrate that a 0.05 difference in FFR between adenosine and UTP with a standard deviation of 0.15-0.17 represents a statistically significant difference (p=0.003).

If we were planning a study of a continuous response variable from matched pairs of study subjects, the prior data indicate that the difference in the response of matched pairs is normally distributed with a standard deviation of 0.16. If the true difference in the mean response of matched pairs is 0.05, we will need to study only 135 pairs of subjects to be able to reject the null hypothesis that this response difference is zero with probability (power) 0.95. The Type I error probability associated with this test of this null hypothesis is 0.05.

| FFR | BL | Adenosine | BL | UTP |
| --- | --- | --- | --- | --- |
| Mean | 0.89 | 0.77 | 0.88 | 0.72 |
| SD | 0.1 | 0.15 | 0.12 | 0.17 |
| 2SD | 0.2 | 0.31 | 0.24 | 0.34 |
| Ttest | | | | 0.0034 |

The cut-off value for FFR is usually 0.8 for being indicative of a treatment intervention being required (according to the set FFR value in the FAME study). This means that if patients have a FFR >0.8, they can be left untreated, however if the value is <0.8, they should be subjected to a PCI with insertion of a stent or bypass surgery according to the lesion anatomy For the guiding catheter study, a FFR set at ≦0.75 or ≦0.8 would require altered treatment regiments in the below percentage of patients with:

| FFR ≦ 0.8 | 240 µg/min (n = 23) |
|---|---|
| Ado (% of patients) | 43% |
| Utp (% of patients) | 65% |
| FFR ≦ 0.75 | |
| Ado (% of patients) | 39% |
| Utp (% of patients) | 47% |

Consequently, by using UTP in accordance with the present invention, it would be possible to diagnose more people than by the known use of adenosine regardless of the set cut-off value for the same concentration.

As seen from the microcatheter study, a FFR set at 50.8 would require altered treatment regiments in the below percentage of patients in the different concentration:

| FFR ≦ 0.8 | 80 µg/min (n = 8) | 160 µg/min (n = 6) | 320 µg/min (n = 9) | 400 µg/min (n = 3) |
|---|---|---|---|---|
| Ado (% of patients) | 37 | 33 | 44 | 33 |
| Utp (% of patients) | 62 | 50 | 44 | 33 |

Although it may seem as if ado=UTP for the higher concentrations, the estimate of FFR is always based on the lowest possible FFR, because only at this point is there maximal hypermia which corresponds to the correct perfusion pressure.

Example 6

(Prophetic) Use of UTP, a Derivative Thereof, or a Salt Thereof to Diagnose Renal Artery Stenosis When a renal arterial stenosis is identified on an arteriogram, intra-arterial systemic pressure can be measured continuously with a transducer and a miniaturized pressure-gradient wire system (PressureWire; St. Jude Medical or Volcano combo wire). Pressures can be recorded using a fiber-optic pressure sensor located laterally and 3 cm from the distal end. The basic principle is that the element modulates an optical reflection with pressure-induced elastic movements. This pressure wire thus replaces a standard 0.018-inch guide wire. After advancing a 4 to 7-F guiding catheter from the femoral artery to the ostium of the renal artery, a "coronary" 0.014-inch wire is introduced into the guiding catheter and moved to the ostium of the stenosis. A pressure gradient across renal arteries can be assessed when combined with an infusion of UTP, a derivative thereof, or a salt thereof to induce renal hyperemia. Infusion of adenosine will, under these circumstances, constrict the afferent arterioles, causing dose-dependent renal vasoconstriction, whereas UTP produces the desired renal vasodilatation. After identical pressure of the guiding catheter and the wire is confirmed at this position, the stenosis can be traversed by means of the floppy-ended wire, followed by the transducer. Dilation equipment can then be inserted through the guiding catheter and across the stenosis, leaving the wire in place. Immediately after the intervention, results can be tested using another infusion of UTP, a derivative thereof, or a salt thereof. The pressure gradient is thus measured with the wire before and during the infusion.

Patients with a renal artery stenosis with a Pd/Pa ratio larger than 0.90 can be considered hemodynamically insignificant, and it is unlikely that renal angioplasty would be useful in such patients even though percent diameter stenosis is larger than 50%. Conversely, renal artery stenoses with a Pd/Pa ratio <0.90 should be considered hemodynamically significant regardless of angiographic severity. Furthermore, a combined catheter with pressure and UTP infusion could ensure a local infusion of the compound to prevent systemic spill over in patients.

All patent and non-patent references cited in the application are hereby incorporated by reference in their entirety.

REFERENCES

WO 2007/065437
U.S. Pat. No. 5,292,498
U.S. Pat. No. 5,789,391
U.S. Pat. No. 5,837,861
1 Erlinge D, Burnstock G: P2 receptors in cardiovascular regulation and disease. Purinergic signalling 2008; 4:1-20.
2 Burnstock G, Ralevic V: New insights into the local regulation of blood flow by perivascular nerves and endothelium. British journal of plastic surgery 1994; 47:527-543.
3 Jeremias A, Filardo S D, Whitbourn R J, Kernoff R S, Yeung A C, Fitzgerald P J, Yock P G: Effects of intravenous and intracoronary adenosine 5'-triphosphate as compared with adenosine on coronary flow and pressure dynamics. Circulation 2000; 101:318-323.
4 Jeremias A, Whitbourn R J, Filardo S D, Fitzgerald P J, Cohen D J, Tuzcu E M, Anderson W D, Abizaid M, Mintz G S, Yeung A C, Kern M J, Yock P G: Adequacy of intracoronary versus intravenous adenosine-induced maximal coronary hyperemia for fractional flow reserve measurements. American heart journal 2000; 140:651-657.
5 Kato M, Shiode N, Teragawa H, Hirao H, Yamada T, Yamagata T, Matsuura H, Kajiyama G: Adenosine 5'-triphosphate induced dilation of human coronary microvessels in vivo. Internal medicine (Tokyo, Japan) 1999; 38:324-329.
6 Sonoda S, Takeuchi M, Nakashima Y, Kuroiwa A: Safety and optimal dose of intracoronary adenosine 5'-triphosphate for the measurement of coronary flow reserve. American heart journal 1998; 135:621-627.
7 Tobis J, Azarbal B, Slavin L: Assessment of intermediate severity coronary lesions in the catheterization laboratory. Journal of the American College of Cardiology 2007; 49:839-848.
8 Yoon M H, Tahk S J, Yang H M, Park J S, Zheng M, Lim H S, Choi B J, Choi S Y, Choi U J, Hwang J W, Kang S J, Hwang G S, Shin J H: Comparison of the intracoronary continuous infusion method using a microcatheter and the intravenous continuous adenosine infusion method for inducing maximal hyperemia for fractional flow reserve measurement. American heart journal 2009; 157:1050-1056.
9 Rosenmeier J B, Yegutkin G G, Gonzalez-Alonso J: Activation of atp/utp-selective receptors increases blood flow and blunts sympathetic vasoconstriction in human skeletal muscle. The Journal of physiology 2008; 586:4993-5002.
10 Rosenmeier J B, Hansen J, Gonzalez-Alonso J: Circulating atp-induced vasodilatation overrides sympathetic vasoconstrictor activity in human skeletal muscle. The Journal of physiology 2004; 558:351-365.

11 Hrafnkelsdottir T, Erlinge D, Jern S: Extracellular nucleotides atp and utp induce a marked acute release of tissue-type plasminogen activator in vivo in man. Thrombosis and haemostasis 2001; 85:875-881.

12 Thaning P, Bune L T, Hellsten Y, Pilegaard H, Saltin B, Rosenmeier J B: Attenuated purinergic receptor function in patients with type 2 diabetes. Diabetes; 59:182-189.

13 Borna C, Wang L, Gudbjartsson T, Karlsson L, Jern S, Malmsjo M, Erlinge D: Contractions in human coronary bypass vessels stimulated by extracellular nucleotides. The Annals of thoracic surgery 2003; 76:50-57.

14 Malmsjo M, Adner M, Harden T K, Pendergast W, Edvinsson L, Erlinge D: The stable pyrimidines udpbetas and utpgammas discriminate between the p2 receptors that mediate vascular contraction and relaxation of the rat mesenteric artery. British journal of pharmacology 2000; 131:51-56.

15 Malmsjo M, Hou M, Harden T K, Pendergast W, Pantev E, Edvinsson L, Erlinge D: Characterization of contractile p2 receptors in human coronary arteries by use of the stable pyrimidines uridine 5'-o-thiodiphosphate and uridine 5'-o-3-thiotriphosphate. The Journal of pharmacology and experimental therapeutics 2000; 293:755-760.

16 Matsumoto T, Nakane T, Chiba S: Utp induces vascular responses in the isolated and perfused canine epicardial coronary artery via utp-preferring p2y receptors. British journal of pharmacology 1997; 122:1625-1632.

17 Seye C I, Kong Q, Erb L, Garrad R C, Krugh B, Wang M, Turner J T, Sturek M, Gonzalez F A, Weisman G A: Functional p2Y2 nucleotide receptors mediate uridine 5'-triphosphate-induced intimal hyperplasia in collared rabbit carotid arteries. Circulation 2002; 106:2720-2726.

18 Shen J, Seye C I, Wang M, Weisman G A, Wilden P A, Sturek M: Cloning, up-regulation, and mitogenic role of porcine p2Y2 receptor in coronary artery smooth muscle cells. Molecular pharmacology 2004; 66:1265-1274.

19 Pillois X, Chaulet H, Belloc I, Dupuch F, Desgranges C, Gadeau A P: Nucleotide receptors involved in utp-induced rat arterial smooth muscle cell migration. Circulation research 2002; 90:678-681.

20 Chaulet H, Desgranges C, Renault M A, Dupuch F, Ezan G, Peiretti F, Loirand G, Pacaud P, Gadeau A P: Extracellular nucleotides induce arterial smooth muscle cell migration via osteopontin. Circulation research 2001; 89:772-778.

21 Seye C I, Yu N, Jain R, Kong Q, Minor T, Newton J, Erb L, Gonzalez F A, Weisman G A: The p2Y2 nucleotide receptor mediates utp-induced vascular cell adhesion molecule-1 expression in coronary artery endothelial cells. The Journal of biological chemistry 2003; 278:24960-24965.

22 Tonino P A, De Bruyne B, Pijls N H, Siebert U, Ikeno F, van' t Veer M, Klauss V, Manoharan G, Engstrom T, Oldroyd K G, Ver Lee P N, MacCarthy P A, Fearon W F: Fractional flow reserve versus angiography for guiding percutaneous coronary intervention. The New England journal of medicine 2009; 360:213-224.

23 McGeoch R J, Oldroyd K G: Pharmacological options for inducing maximal hyperaemia during studies of coronary physiology. Catheter Cardiovasc Interv 2008; 71:198-204.

24 De Bruyne B, Manoharan G, Pijls N H, Verhamme K, Madaric J, Bartunek J, Vanderheyden M, Heyndrickx G R: Assessment of renal artery stenosis severity by pressure gradient measurements. Journal of the American College of Cardiology 2006; 48:1851-1855.

25 Trochu J N, Zhao G, Post H, Xu X, Belardinelli L, Belloni F L, Hintze T H: Selective a2a adenosine receptor agonist as a coronary vasodilator in conscious dogs: Potential for use in myocardial perfusion imaging. Journal of cardiovascular pharmacology 2003; 41:132-139.

26 Wangensteen R, Fernandez O, Sainz J, Quesada A, Vargas F, Osuna A: Contribution of endothelium-derived relaxing factors to p2y-purinoceptor-induced vasodilation in the isolated rat kidney. General pharmacology 2000; 35:129-133.

27 Ko H, Carter R L, Cosyn L, Petrelli R, de Castro S, Besada P, Zhou Y, Cappellacci L, Franchetti P, Grifantini M, Van Calenbergh S, Harden T K, Jacobson K A: Synthesis and potency of novel uracil nucleotides and derivatives as p2y2 and p2y6 receptor agonists. Bioorganic & medicinal chemistry 2008; 16:6319-6332.

28 Bokhari S, Ficaro E P, McCallister B D, Jr.: Adenosine stress protocols for myocardial perfusion imaging. J Nucl Cardiol 2007; 14:415-416.

29 Futamatsu H, Wilke N, Klassen C, Angiolillo D J, Suzuki N, Kawaguchi R, Shoemaker S, Siuciak A, Bass T A, Costa M A: Usefulness of cardiac magnetic resonance imaging for coronary artery disease detection. Minerva cardioangiologica 2007; 55:105-114.

30 Douglas P S, Khandheria B, Stainback R F, Weissman N J, Peterson E D, Hendel R C, Stainback R F, Blaivas M, Des Prez R D, Gillam L D, Golash T, Hiratzka L F, Kussmaul W G, Labovitz A J, Lindenfeld J, Masoudi F A, Mayo P H, Porembka D, Spertus J A, Wann L S, Wiegers S E, Brindis R G, Douglas P S, Hendel R C, Patel M R, Peterson E D, Wolk M J, Allen J M: Accf/ase/acep/aha/asnc/scai/scct/scmr 2008 appropriateness criteria for stress echocardiography: A report of the american college of cardiology foundation appropriateness criteria task force, american society of echocardiography, american college of emergency physicians, american heart association, american society of nuclear cardiology, society for cardiovascular angiography and interventions, society of cardiovascular computed tomography, and society for cardiovascular magnetic resonance endorsed by the heart rhythm society and the society of critical care medicine. Journal of the American College of Cardiology 2008; 51:1127-1147.

31 Beanlands R S, Chow B J, Dick A, Friedrich M G, Gulenchyn K Y, Kiess M, Leong-Poi H, Miller R M, Nichol G, Freeman M, Bogaty P, Honos G, Hudon G, Wisenberg G, Van Berkom J, Williams K, Yoshinaga K, Graham J: Ccs/car/canm/cncs/canscmr joint position statement on advanced noninvasive cardiac imaging using positron emission tomography, magnetic resonance imaging and multidetector computed tomographic angiography in the diagnosis and evaluation of ischemic heart disease—executive summary. The Canadian journal of cardiology 2007; 23:107-119.

The invention claimed is:

1. A method for determining whether blood flow is restricted in a blood vessel of an individual suspected of compromised blood flow in the vessel, the method comprising:
(a) delivering UTP, a derivative thereof, or a salt thereof, wherein the UTP, a derivative thereof, or a salt thereof, is selected from the group consisting of UTP, UTPγS, MRS2498, uridine 5'-trisphosphate tris salt, uridine 5'-trisphosphate salt dihydrate, uridine 5'-trisphosphate salt solution, uridine 5'-trisphosphate salt hydrate, uridine-$^{13}C_9$, $^{15}N_2$ 5'-trisphosphate sodium salt solution, uridine-$^{15}N_2$ 5'-trisphosphate sodium salt solution, uridine 5'-triphosphate trisodium salt hydrate, uridine-$^{13}C_9$, $^{15}N_2$ 5'-triphosphate sodium salt solution uridine-$^{15}N_2$ 5'-triphosphate sodium salt solution 2-diuridine tetraphosphate, thioUTP tetrasodium salt, denufosol tetrasodium, and UTPyS trisodium salt,
to said vessel,
(b) assessing blood flow quantitatively in the vessel by obtaining a value that correlates to blood flow in said vessel,
(c) comparing the obtained value with a reference value, and
(d) determining whether the individual has compromised blood flow based on whether there is a difference between the obtained value and the reference value indicative of a reduction in blood flow relative to a healthy vessel.

2. The method of claim 1, wherein the individual is suffering or suspected to be suffering from atherosclerosis or vascular stenosis.

3. The method of claim 1 wherein said individual is suffering or is suspected to be suffering of Peripheral Artery Disease (PAD), coronary atherosclerosis, atherosclerosis, renal artery stenosis, or ischemic heart disease.

4. The method of claim 1, wherein the reference value is obtained by measuring blood flow in another similar vessel of said individual.

5. The method of claim 1, wherein blood flow is assessed by FFR or CFR measurement.

6. The method of claim 1, wherein UTP, a derivative thereof, or a salt thereof is delivered by in situ infusion.

7. The method of claim 1, wherein the UTP, a derivative thereof, or a salt thereof, is administered at a rate of infusion from about 50 to about 400 µg of the compound per minute.

8. The method of claim 1, wherein the UTP, a derivative thereof, or a salt thereof, is administered via continuous intravenous infusion, intracoronary infusion, drip infusion, intracoronary bolus injection, a guiding catheter, or an IC microcatheter.

9. The method of claim 8, wherein the UTP, a derivative thereof, or a salt thereof, is administered via a guiding catheter or an IC microcatheter.

10. The method of claim 8, wherein the UTP, a derivative thereof, or a salt thereof, is administered at a rate of infusion is about 80 to about 360 µg of the compound per minute.

11. The method of claim 1, wherein the compromised blood flow results from a blood clot or stenosis.

12. A method for diagnosing renal artery stenosis comprising:
(a) delivering UTP, a derivative thereof, or a salt thereof, wherein
the UTP, a derivative thereof, or a salt thereof, is selected from the group consisting of UTP, UTPyS, MRS2498, uridine 5'-trisphosphate tris salt, uridine 5'-trisphosphate salt dihydrate, uridine 5'-trisphosphate salt solution, uridine 5'-trisphosphate salt hydrate uridine-$^{13}C_9$, $^{15}N_2$ 5'-trisphosphate sodium salt solution uridine-$^{15}N_2$ 5'-trisphosphate sodium salt solution uridine 5'-triphosphate trisodium salt hydrate uridine-$^{13}C_9$, $^{15}N_2$ 5'-triphosphate sodium salt solution uridine-$^{15}N_2$ 5'-triphosphate sodium salt solution, 2-diuridine tetraphosphate, thioUTP tetrasodium salt, denufosol tetrasodium, and UTPyS trisodium salt,
to an individual suspected of having said disease,
(b) assessing blood flow quantitatively in the vessel by obtaining a value that correlates to blood flow in said vessel,
(c) comparing the obtained value with a reference value, and
(d) determining whether the individual has compromised blood flow based on the results of the comparison.

* * * * *